US011725208B2

(12) United States Patent
Oestergaard et al.

(10) Patent No.: US 11,725,208 B2
(45) Date of Patent: Aug. 15, 2023

(54) CONJUGATED ANTISENSE COMPOUNDS AND THEIR USE

(71) Applicant: Ionis Pharmaceuticals, Inc., Carlsbad, CA (US)

(72) Inventors: Michael Oestergaard, Carlsbad, CA (US); Punit P. Seth, Carlsbad, CA (US); Frank Rigo, Carlsbad, CA (US); Chrissa A. Dwyer, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 62 days.

(21) Appl. No.: 16/771,620

(22) PCT Filed: Dec. 14, 2018

(86) PCT No.: PCT/US2018/065830
§ 371 (c)(1),
(2) Date: Jun. 10, 2020

(87) PCT Pub. No.: WO2019/118916
PCT Pub. Date: Jun. 20, 2019

(65) Prior Publication Data
US 2020/0392509 A1   Dec. 17, 2020

Related U.S. Application Data

(60) Provisional application No. 62/598,926, filed on Dec. 14, 2017.

(51) Int. Cl.
*C12N 15/113* (2010.01)
*A61K 9/00* (2006.01)

(52) U.S. Cl.
CPC ........ *C12N 15/1137* (2013.01); *A61K 9/0085* (2013.01); *C12N 15/113* (2013.01); *C12N 2310/11* (2013.01); *C12N 2310/113* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/351* (2013.01); *C12N 2310/3515* (2013.01); *C12N 2310/3535* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 12/1993 | Summerton et al. |
| 5,367,066 A | 11/1994 | Urdea et al. |
| 5,432,272 A | 7/1995 | Benner |
| 5,434,257 A | 7/1995 | Matteucci |
| 5,457,187 A | 10/1995 | Gmelner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,587,470 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 6,005,087 A | 12/1999 | Cook et al. |

(Continued)

FOREIGN PATENT DOCUMENTS

WO  WO 1999/014226  3/1999
WO  WO 2004/044132  5/2004

(Continued)

OTHER PUBLICATIONS

Asami et al., "Drug delivery system of therapeutic oligonucleotides" Drug Discov Ther (2016) 10: 256-262.
Asami et al., "Efficient Gene Suppression by DNA/DNA Double-Stranded Oligonucleotide In Vivo" Mol Ther (2021) 29: 838-847.
Extended EP Search Report for 18888580.0 dated Sep. 1, 2021, 6 pages.
Nishina et al., "DNA/RNA heteroduplex oligonucleotide for highly efficient gene silencing" Nat Commun (2015) 10: 1-13.
Yokota "DNA/RNA heteroduplex oligonucleotide for highly efficient gene silencing" Clin Experiment Neurolimmunol (2016) 7: 108-109.
Albaek et al., "Analogues of a locked nucleic acid with three-carbon 2',4'-linkages: synthesis by ring-closing metathesis and influence on nucleic acid duplex stability and structure" J. Org. Chem. (2006) 71: 7731-7740.

(Continued)

*Primary Examiner* — Sean McGarry
(74) *Attorney, Agent, or Firm* — McNeill Baur PLLC

(57) ABSTRACT

The present disclosure provides half duplex compounds comprising a first oligomeric compound and a second, shorter, oligomeric compound, wherein the first oligomeric compound is complementary to a target nucleic acid and the second oligomeric compound is complementary to the first oligomeric compound. In certain embodiments, the compounds disclosed herein are useful for modulating the expression of extra-hepatic target nucleic acids.

33 Claims, No Drawings

Specification includes a Sequence Listing.

(56) References Cited

U.S. PATENT DOCUMENTS

| | | | |
|---|---|---|---|
| 6,005,096 | A | 12/1999 | Matteucci et al. |
| 6,166,199 | A | 12/2000 | Cook et al. |
| 6,268,490 | B1 | 7/2001 | Imanishi et al. |
| 6,525,191 | B1 | 2/2003 | Ramasamy |
| 6,531,584 | B1 | 3/2003 | Cook et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,666,854 | B2 | 2/2010 | Seth et al. |
| 7,696,345 | B2 | 4/2010 | Allerson et al. |
| 7,741,457 | B2 | 6/2010 | Swayze et al. |
| 7,750,131 | B2 | 7/2010 | Seth et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,124,745 | B2 | 2/2012 | Allerson et al. |
| 8,153,365 | B2 | 4/2012 | Wengel et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,501,805 | B2 | 4/2013 | Seth et al. |
| 8,440,803 | B2 | 5/2013 | Swayze et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,796,437 | B2 | 8/2014 | Swayze et al. |
| 9,005,906 | B2 | 4/2015 | Swayze et al. |
| 9,012,421 | B2 | 4/2015 | Migawa et al. |
| 2003/0158403 | A1 | 8/2003 | Manoharan et al. |
| 2003/0175906 | A1 | 9/2003 | Manoharan et al. |
| 2004/0014956 | A1* | 1/2004 | Woolf .............. C12N 15/113 536/23.1 |
| 2008/0039618 | A1 | 2/2008 | Allerson et al. |
| 2013/0203836 | A1 | 8/2013 | Rajeev et al. |
| 2015/0191727 | A1 | 7/2015 | Migawa et al. |
| 2018/0258425 | A1 | 9/2018 | Rigo et al. |

FOREIGN PATENT DOCUMENTS

| | | |
|---|---|---|
| WO | WO 2004/106356 | 12/2004 |
| WO | WO 2007/134181 | 11/2007 |
| WO | WO 2008/101157 | 8/2008 |
| WO | WO 2011/133876 | 10/2011 |
| WO | 2014132671 A1 | 9/2014 |
| WO | WO 2014/179620 | 11/2014 |
| WO | 2014192310 A1 | 12/2014 |
| WO | 2015105083 A1 | 7/2015 |
| WO | WO 2015/106128 | 7/2015 |
| WO | WO 2016/077704 | 5/2016 |
| WO | WO 2017/053995 | 3/2017 |
| WO | WO 2019/118916 | 6/2019 |

OTHER PUBLICATIONS

Braasch et al., "Novel antisense and peptide nucleic acid strategies for controlling gene expression" Biochemistry (2002) 41: 4503-4510.

Crooke "Antisense Drug Technology" Crooke S.T., Ed., CRC Press (2008) 163-166 and 442-443.

Crooke et al., "Pharmacokinetic properties of several novel oligonucleotide analogs in mice" J. Pharmacol. Exp. Ther. (1996) 277: 923-937.

Freier et al., "The ups and downs of nucleic acid duplex stability: structure-stability studies on chemically-modified DNA:RNA duplexes" Nucleic Acids Research (1997) 25(22): 4429-4443.

Ereden et al., "Expanding the design horizon of antisense oligonucleotides with alpha-L-LNA" Nucleic Acids Research (2003) 21: 6365-6372.

International Search Report for PCT/US18/065830 dated Mar. 7, 2019.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259: 327-330.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.

Kumar et al., "The first analogues of LNA (Locked Nucleic Acids): Phosphorothioate-LNA and 2'-THIO-LNA" Bioorg. Med. Chem. Lett. (1998) 8: 2219-2222.

Kumar et al., Design, synthesis, biophysical and primer extension studies of novel acyclic butyl nucleic acid (BuNA) Org. Biomol. Chem. (2013) 11: 5853-5865.

Letsinger et al., "Cholesteryl-conjugated oligonucleotides: Synthesis, properties, and activity as inhibitors of replication of human immunodeficiency virus in cell culture" Proc. Natl. Acad. Sci. USA (1989) 86: 6553-6556.

Leumann "DNA Analogues: From Supramolecular Principles to Biological Properties" CJ. Bioorg. & Med. Chem. (2002) 10: 841-854.

Manoharan et al., "Cholic Acid-Oligonucleotide Conjugates for Antisense Applications" Bioorg. Med. Chem. Lett. (1994) 4:1053-1060.

Manoharan et al., "Chemical Modifications to Improve Uptake and Bioavailability of Antisense Oligonucleotides" Ann. N.Y. Acad. Sci. (1992) 660: 306-309.

Manoharan et al., "Introduction of a Lipophilic Thioether Tether in the Minor Groove of Nucleic Acids for Antisense Applications" Bioorg. Med. Chem. Lett. (1993) 3(12): 2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5): 969-973.

Mishra et al., "Improved leishmanicidal effect of phosphorotioate antisense oligonucleotides by LDL-mediated delivery" Biochim. Biophys. Acta (1995) 1264:229-237.

Nishina et al., "Chimeric Antisense Oligonucleotide Conjugated to alpha-Tocopherol" Molecular Therapy Nucleic Acids (2015) 4:e220.

Nishina et al., "Efficient In Vivo Delivery of siRNA to the liver by Conjugation of alpha-Tocopherol." Molecular Therapy (2008) 16(4): 734-740.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Shea et al., "Synthesis, hybridization properties and antiviral activity of lipid-oligodeoxy nucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

(56) References Cited

OTHER PUBLICATIONS

Svinarchuk et al., "Inhibition of HIV proliferation in MT-4 cells by antisense oligonucleotide conjugated to lipophilic groups" Biochimie (1993) 75:49-54.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

* cited by examiner

SEQUENCE LISTING

<160> NUMBER OF SEQ ID NOS: 19

<210> SEQ ID NO 1
<211> LENGTH: 14411
<212> TYPE: DNA
<213> ORGANISM: Homo sapien

<400> SEQUENCE: 1

```
ctcccagccc agcgcctccc acccctttc atagcaggaa aagccggagc ccagggaggg      60
aacggacctg cgagtcacac aactggtgac ccacaccagc ggctggagca ggaccctctt    120
ggggagaaga gcatcctgcc cgcagccagg gcccctcatc aaagtcctcg gtgtttttta    180
aattatcaga actgcccagg accacgtttc ccaggccctg cccagctggg actcctcggt    240
ccttgcctcc tagtttctca ggcctggccc tctcaaggcc caggcacccc aggccggttg    300
gaggccccga cttccactct ggagaaccgt ccaccctgga aagaagagct cagattcctc    360
ttggctctcg gagccgcagg gagtgtgtct tcccgcgcca ccctccaccc cccgaaatgt    420
ttctgtttct aatcccagcc tgggcaggaa tgtggctccc cggccagggg ccaaggagct    480
```

```
                                                           -continued attttggggt ctcgtttgcc cagggagggc ttggctccac cactttcctc ccccagcctt    540
tgggcagcag gtcacccctg ttcaggctct gagggtgccc cctcctggtc ctgtcctcac    600
caccccttcc ccacctcctg ggaaaaaaaa aaaaaaaaa aaaaaagct ggtataaagc      660 agagagcctg agggctaaat ttaactgtcc gagtcggaat ccatctctga gtcacccaag    720
aagctgccct ggcctcccgt cccttcccca ggcctcaacc cctttctccc acccagcccc    780 aaccccagc cctcacccccc tagccccag ttctggagct tgtcgggagc aagggggtgg     840
ttgctactgg gtcactcagc tcaattggcc ctgtttcag caatgggcag gttcttcttg     900
aaattcatca cacctgtggc ttcctctgtg ctctaccttt ttattggggt gacagtgtga    960
cagctgagat tctccatgca ttcccctac tctagcactg aagggttctg aagggccctg    1020
gaaggaggga gcttgggggg ctggcttgtg aggggttaag gctgggaggc gggagggggg   1080
ctggaccaag gggtggggag aaggggagga ggcctcggcc ggccgcagag agaagtggcc   1140
agagaggccc aggggacagc cagggacagg cagacatgca gccagggctc cagggcctgg   1200
acaggggctg ccaggccctg tgacaggagg accccgagcc cccggcccgg ggaggggcca   1260
tggtgctgcc tgtccaacat gtcagccgag gtgcggctga ggcggctcca gcagctggtg   1320
ttggacccgg gcttcctggg gctggagccc ctgctcgacc ttctcctggg cgtccaccag   1380
gagctgggcg cctccgaact ggcccaggac aagtacgtgg ccgacttctt gcagtggggt   1440
gagtgcctac cctcggggct cctgcagatg gggtgggggt ggggcaggag acaggtctgg   1500 gcacagagc ctggctgttg ggggggcagg atggcaggat gggcatgggg agatcctccc    1560
atcctggggc tcagagtgtg gacctgggcc ctggggcaac atttctctgt cctatgccac   1620
cactctggag gggcagagta aggtcagcag aggctagggt ggctgtgact cagagccatg   1680
gcttaggagt cacagcaggc taggctgcca acagcctccc atggcctctc tgcaccccgc   1740
ctcagggtca gggtcaggt catgctggga gctccctctc ctaggaccct ccccccaaaa    1800
gtgggctcta tggccctctc ccctggtttc ctgtggcctg ggcaagcca ggagggccag    1860 catgggcag ctgccagggg cgcagccgac aggcaggtgt tcggcgccag cctctccagc    1920
tgccccaaca ggtgcccagg cactgggagg gcggtgactc acgcgggccc tgtgggagaa   1980
ccagctttgc agacaggcgc caccagtgcc ccctcctctg cgatccagga gggacaactt   2040
tgggttcttc tgggtgtgtc tccttctttt gtaggttctg cacccacccc caccccagc    2100 cccaaagtct cggttcctat gagccgtgtg ggtcagccac cattcccgcc accccgggtc   2160
cctgcgtcct ttagttctcc tggcccaggg cctccaacct tccagctgtc ccacaaaacc   2220
ccttcttgca agggctttcc agggcctggg gccagggctg aaggaggat gcttccgctt    2280 ctgccagctg ccttgtctgc ccacctcctc cccaagccca ggactcgggc tcactggtca   2340
ctggtttctt tcattcccag caccctgccc ctctggccct catatgtctg gccctcagtg   2400
actggtgttt ggttttggc ctgtgtgtaa caaactgtgt gtgacacttg tttcctgttt    2460
ctccgccttc ccctgcttcc tcttgtgtcc atctctttct gacccaggcc tggttccttt   2520
ccctcctcct cccatttcac agatgggaag gtggaggcca agaagggcca ggccattcag   2580
cctctggaaa aaccttctcc caacctccca cagcccctaa tgactctcct ggcctcccct   2640
tagtagagga tgaagttggg ttggcagggt aaactgagac cgggtggggt aggggtctgg   2700
cgctcccggg aggagcactc cttttgtggc ccgagctgca tctcgcggcc ctcccctgc    2760 caggcctggg gcggggagg gggccagggt tcctgctgcc ttaaaagggc tcaatgtctt    2820
```

```
ggctctctcc tccctccccc gtcctcagcc ctggctggtt cgtccctgct ggcccactct   2880
cccggaaccc cccggaaccc ctctctttcc tccagaaccc actgtctcct ctccttccct   2940
cccctcccat acccatccct ctctccatcc tgcctccact tcttccaccc ccgggagtcc   3000
aggcctccct gtccccacag tccctgagcc acaagcctcc accccagctg gtcccccacc   3060
caggctgccc agtttaacat tcctagtcat aggaccttga cttctgagag gcctgattgt   3120
catctgtaaa taaggggtag gactaaagca ctcctcctgg aggactgaga gatgggctgg   3180
accggagcac ttgagtctgg gatatgtgac catgctacct ttgtctccct gtcctgttcc   3240
ttcccccagc cccaaatcca ggttttccca agtgtggtt caagaaccac ctgcatctga   3300
atctagaggt actggataca accccacgtc tgggccgtta cccaggacat tctacatgag   3360
aacgtggggg tggggccctg gctgcacctg aactgtcacc tggagtcagg gtggaaggtg   3420
gaagaactgg gtcttatttc cttctcccct tgttctttag ggtctgtcct tctgcagact   3480
ccgttacccc accctaacca tcctgcacac ccttggagcc ctctgggcca atgccctgtc   3540
ccgcaaaggg cttctcaggc atctcacctc tatgggaggg cattttggc ccccagaacc   3600 ttacacggtg tttatgtggg gaagcccctg ggaagcagac agtcctaggg tgaagctgag   3660
aggcagagag aaggggagac agacagaggg tggggcttc cccttgtct ccagtgccct   3720 ttctggtgac cctcggttct tttccccac cacccccca gcggagccca tcgtggtgag   3780
gcttaaggag gtccgactgc agaggacga cttcgagatt ctgaaggtga tcggacgcgg   3840
ggcgttcagc gaggtaagcc gaaccgggcg ggagcctgac ttgactcgtg gtgggcgggg   3900 catagggggtt ggggcgggc cttagaaatt gatgaatgac cgagccttag aacctagggc   3960
tgggctggag gcgggcttg ggaccaatgg gcgtggtgtg gcaggtgggg cggggccacg   4020
gctgggtgca gaagcgggtg gagttgggtc tgggcgagcc cttttgtttt cccgccgtct   4080
ccactctgtc tcactatctc gacctcaggt agcggtagtg aagatgaagc agacgggcca   4140
ggtgtatgcc atgaagatca tgaacaagtg ggacatgctg aagaggggcg aggtgagggg   4200
ctgggcggac gtgggggct tgaggatcc gcgccccgtc tccggctgca gctcctccgg   4260
gtgccctgca ggtgtcgtgc ttccgtgagg agagggacgt gttggtgaat ggggaccggc   4320
ggtggatcac gcagctgcac ttcgccttcc aggatgagaa ctacctggtg agctccgggc   4380
cggggtgact aggaagaggg acaagagccc gtgctgtcac tggacgagga ggtggggaga   4440
ggaagctcta ggattggggg tgctgcccgg aaacgtctgt gggaaagtct gtgtgcggta   4500
agagggtgtg tcaggtggat gagggccctt ccctatctga gacggggatg gtgtccttca   4560
ctgcccgttt ctggggtgat ctgggggact cttataaaga tgtctctgtt gcgggggtc   4620 tcttacctgg aatgggatag gtcttcagga attctaacgg ggccactgcc tagggaagga   4680
gtgtctggga cctattctct gggtgttggg tggcctctgg gttctctttc ccagaacatc   4740
tcagggggag tgaatctgcc cagtgacatc ccaggaaagt ttttttgttt gtgttttttt   4800 ttgagggcg ggcgggggg ccgcaggtgg tctctgattt ggcccggcag atctctatgg   4860
ttatctctgg gctggggctg caggtctctg cccaaggatg gggtgtctct gggaggggtt   4920
gtcccagcca tccgtgatgg atcagggcct caggggacta ccaaccaccc atgacgaacc   4980
ccttctcagt acctggtcat ggagtattac gtgggcgggg acctgctgac actgctgagc   5040
aagtttgggg agcggattcc ggccgagatg gcgcgcttct acctggcgga gattgtcatg   5100
gccatagact cggtgcaccg gcttggctac gtgcacaggt gggtgcagca tggccgaggg   5160
gatagcaagc ttgttccctg gccgggttct tggaaggtca gagcccagag aggccagggc   5220
```

```
ctggagaggg accttcttgg ttggggccca ccgggggtg cctgggagta ggggtcagaa   5280
ctgtagaagc cctacagggg cggaacccga ggaagtgggg tcccaggtgg cactgccgg   5340 aggggcggag cctggtggga ccacagaagg gaggttcatt tatcccaccc ttctcttttc   5400
ctccgtgcag ggacatcaaa cccgacaaca tcctgctgga ccgctgtggc cacatccgcc   5460
tggccgactt cggctcttgc ctcaagctgc gggcagatgg aacggtgagc cagtgccctg   5520
gccacagagc aactggggct gctgatgagg gatggaaggc acagagtgtg ggagcgggac   5580
tggatttgga ggggaaaaga ggtggtgtga cccaggctta agtgtgcatc tgtgtggcgg   5640
agtattagac caggcagagg gaggggctaa gcatttgggg agtggttgga aggagggccc   5700
agagctggtg ggcccagagg ggtgggccca agcctcgctc tgctcctttt ggtccaggtg   5760
cggtcgctgg tggctgtggg cacccagac tacctgtccc ccgagatcct gcaggctgtg   5820
ggcggtgggc ctgggacagg cagctacggg cccgagtgtg actggtgggc gctgggtgta   5880
ttcgcctatg aaatgttcta tgggcagacg cccttctacg cggattccac ggcggagacc   5940
tatggcaaga tcgtccacta caaggtgagc acggccgcag ggagacctgg cctctcccgg   6000
taggcgctcc caggctatcg cctcctctcc ctctgagcag gagcacctct ctctgccgct   6060
ggtggacgaa ggggtccctg aggaggctcg agacttcatt cagcggttgc tgtgtccccc   6120
ggagacacgg ctgggccggg gtggagcagg cgacttccgg acacatccct tcttctttgg   6180
cctcgactgg gatggtctcc gggacagcgt gccccccttt acaccggatt cgaaggtgc   6240 caccgacaca tgcaacttcg acttggtgga ggacgggctc actgccatgg tgagcggggg   6300
cggggtaggt acctgtggcc cctgctcggc tgcgggaacc tccccatgct ccctccataa   6360
agttggagta aggacagtgc ctaccttctg gggtcctgaa tcactcattc cccagagcac   6420
ctgctctgtg cccatctact actgaggacc cagcagtgac ctagacttac agtccagtgg   6480
gggaacacag agcagtcttc agacagtaag gccccagagt gatcagggct gagacaatgg   6540
agtgcagggg gtgggggact cctgactcag caaggaaggt cctggagggc tttctggagt   6600
ggggagctat ctgagctgag acttggaggg atgagaagca ggagaggact cctcctccct   6660
taggccgtct ctcttcaccg tgtaacaagc tgtcatggca tgcttgctcg gctctgggtg   6720
cccttttgct gaacaatact ggggatccag cacggaccag atgagctctg gtccctgccc   6780
tcatccagtt gcagtctaga gaattagaga attatgagaa gtgtggcagg tgccctgaag   6840
ggaagcaaca ggatacaaga aaaaatgatg gggccaggca cggtggctca cgcctgtaac   6900
cccagcaatt tggcaggccg aagtgggtgg attgcttgag cccaggagtt cgagaccagc   6960
ctgggcaatg tggtgagacc ccgtctctca caaaaatgtt ttaaaaattg gttgggcgtg   7020
gtggcgcatg cctgtatact cagctactag ggtggccgac gtgggcttga gcccaggagg   7080
tcaaggctgc agtgagctgt gattgtgcca ctgcactcca gcctgggcaa cggagagaga   7140
ctctgtctca aaataagat aaactgaaat taaaaatag gctgggctgg ccgggcgtgg   7200
tggctcacgc ctgtaatctc agcactttgg gaggccgagg cgggtggatc acgaggtcag   7260
gagatcgaga ccatcttggc taacacggtg aaaccccatc tctcctaaaa atacaaaaaa   7320
ttagccaggc gtggtggcgg cgcctgtag tcccagctac tcaggaggct gaggcaggag   7380
aatggcgtga acccgggagg cagagtttgc agtgagccga gatcgtgcca ctgcactcca   7440
gcctgggcga cagagcgaga ctctgtctca gaaaaaaaaa aaaaaaaaaa aaaaaatagg   7500
ctggaccgcg gccgggcgct gtggctcatg cctgtaatcc cagcactttg ggagtccaag   7560
```

```
gccggtgggt catgagatca ggagttttga gactaggctg gccaacacgg tgaaacccccg    7620
tctctactaa aaatacaaga aaattagctg ggtgtggtct cgggtgcctg taattccagt    7680
tactgggaa gctgaggcag gagaattgct tgaacctggg aggcagagtt tgcagtgagc     7740
caagatcatg ccactacact ccagtctggg tgacagagtg agactctgtc tcaaaaaaaa    7800
aaaaaaaaa aagggttggg caaggtggtt cacgcctgta atcccagaac tttgggaggc     7860
tgaggcaggc agatcactgg aagtcaggag ttcaagacca gcctggccaa catggtgaaa    7920
ccctgtgtct actaaaaata caaaatttag ccaggcttgg tggcgtatgc ctgtaatgcc    7980
agctactcag gaggctgagg caggagaatc gcttgattga acctgggagg cagagtttgc    8040
agtgggctgg ggttgtgcca ctgcactcta ggctgggaga cagcaagact ccatctaaaa    8100
aaaaaaaaca gaactgggct gggcacagtg gcttatattt gtaatcccag cactttggga    8160
ggctgaggtt ggaggactgc ttgagcccag agtttggac tacaacagct gaggtaggcg     8220
gatcacttga ggtcagaaga tggagaccag cctggccagc gtggcgaaac cccgtctcta    8280
ccaaaaatat aaaaaattag ccaggcgtgg tagagggcgc ctgtaatctc agctactcag    8340
gacgctgagg caggagaatc gcctgaacct gggaggcgga ggttgcagtg agctgagatt    8400
gcaccactgc actccagcct gggtaacaga gcgagactcc gtatcaaaga aaagaaaaa    8460
agaaaaaatg ctggaggggc cactttagat aagccctgag ttgggctgg tttggggga     8520
acatgtaagc caagatcaaa aagcagtgag gggcccgccc tgacgactgc tgctcacatc    8580
tgtgtgtctt gcgcaggaga cactgtcgga cattcgggaa ggtgcgccgc taggggtcca    8640
cctgcctttt gtgggctact cctactcctg catggccctc aggtaagcac tgccctggac    8700
ggcctccagg ggccacgagg ctgcttgagc ttcctgggtc ctgctccttg gcagccaatg    8760
gagttgcagg atcagtcttg gaaccttact gttttgggcc caaagactcc taagaggcca    8820
gagttggagg accttaaatt ttcagatcta tgtacttcaa aatgttagat tgaattttaa    8880
aacctcagag tcacagactg gcttcccag aatcttgtaa ccattaactt ttacgtctgt     8940
agtacacaga gccacaggac ttcagaactt ggaaaatatg aagtttagac ttttacaatc    9000
agttgtaaaa gaatgcaaat tctttgaatc agccatataa caataaggcc atttaaaagt    9060
attaatttag gcgggccgcg gtggctcacg cctgtaatcc tagcactttg ggaggccaag    9120
gcaggtggat catgaggtca ggagatcgag accatcctgg ctaacacggt gaaaccccgt    9180
ctctactaaa aatacaaaaa aattagccgg gcatggtggc gggcgcttgc ggtcccagct    9240
acttgggagg cgaggcagga gaatggcatg aacccgggag gcggagcttg cagtgagccg    9300
agatcatgcc actgcactcc agcctgggcg acagagcaag actccgtctc aaaaaaaaaa    9360
aaaaaaagt atttatttag gccggtgtg gtggctcacg cctgtaattc cagtgctttg     9420
ggaggatgag gtgggtggat cacctgaggt caggagttcg agaccagcct gaccaacgtg    9480
gagaaacctc atctctacta aaaacaaaa ttagccaggc gtggtggcat atacctgtaa    9540
tcccagctac tcaggaggct gaggcaggag aatcagaacc caggaggggg aggttgtggt    9600
gagctgagat cgtgccattg cattccagcc tgggcaacaa gagtgaaact tcatctcaaa    9660
aaaaaaaaaa aaaagtact aatttacagg ctgggcatgg tggctcacgc ttggaatccc     9720
agcactttgg gaggctgaag tggacggatt gcttcagccc aggagttcaa gaccagcctg    9780
agcaacataa tgagaccctg tctctacaaa aaattgaaaa aatcgtgcca ggcatggtgg    9840
tctgtgcctg cagtcctagc tactcaggag tctgaagtag gagaatcact tgagcctgga    9900
gtttgaggct tcagtgagcc atgatagatt ccagcctagg caacaaagtg agacctggtc    9960
```

```
tcaacaaaag tattaattac acaaataatg cattgcttat cacaagtaaa ttagaaaata   10020
cagataagga aaaggaagtt gatatctcgt gagctcacca gatggcagtg gtccctggct   10080
cacacgtgta ctgacacatg tttaaatagt ggagaacagg tgttttttg gtttgttttt    10140 ttccccttcc tcatgctact ttgtctaaga aacagttgg ttttctagtc agcttttatt     10200
actggacaac attacacata ctataccta tcattaatga actccagctt gattctgaac    10260
cgctgcgggg cctgaacggt gggtcaggat tgaacccatc ctctattaga acccaggcgc   10320
atgtccagga tagctaggtc ctgagccgtg ttcccacagg agggactgct gggttggagg   10380
ggacagccac ttcatacccc agggaggagc tgtccccttc ccacagctga gtggggtgtg   10440
ctgacctcaa gttgccatct tggggtccca tgccagtct taggaccaca tctgtggagg    10500
tggccagagc caagcagtct ccccatcagg tcggcctccc tgtcctgagg ccctgagaag   10560
aggggtctgc agcggtcaca tgtcaaggga ggagatgagc tgaccctaga acatgggggt   10620 ctggaccca agtccctgca gaaggtttag aaagagcagc tcccagggc ccaaggccag     10680 gagaggggca gggcttttcc taagcagagg aggggctatt ggcctacctg gactctgtt    10740 ctcttcgctc tgctgctccc cttcctcaaa tcaggaggtc ttggaagcag ctgccctac    10800 ccacaggcca gaagttctgg ttctccacca gagaatcagc attctgtctc cctccccact   10860
ccctcctcct ctccccaggg acagtgaggt cccaggcccc acaccatgg aactggaggc    10920 cgagcagctg cttgagccac acgtgcaagc gcccagcctg gagccctcgg tgtccccaca   10980
ggatgaaaca gtaagttggt ggagggagg gggtccgtca gggacaattg ggagagaaaa    11040
ggtgagggct cccgggtgg cgtgcactgt agagccctct agggacttcc tgaacagaag    11100
cagacagaaa ccacggagag acgaggttac ttcagacatg ggacggtctc tgtagttaca   11160
gtggggcatt aagtaagggt gtgtgtgttg ctggggatct gagaagtcga tctttgagct   11220
gagcgctggt gaaggagaaa caagccatg aaggaaaggt gccaagtggt caggcgagag    11280 cctccaggc aaaggccttg ggcaggtggg aatcctgatt tgttcctgaa aggtagtttg    11340
gctgaatcat tcctgagaag gctggagagg ccagcaggaa acaaaaccca gcaaggcctt   11400
ttgtcgtgag ggcattaggg agctggaggg attttgagca gcagagggac ataggttgtg   11460
ttagtgtttg agcaccagcc ctctggtccc tgtgtagatt tagaggacca gactcaggga   11520
tggggctgag gaaggtaggg aagggagggg gcttggatca ttgcaggagc tatgggatt    11580 ccagaaatgt tgagggacg gaggagtagg ggataaacaa ggattcctag cctggaacca    11640
gtgcccaagt cctgagtctt ccaggagcca caggcagcct taagcctggt ccccatacac   11700
aggctgaagt ggcagttcca gcggctgtcc ctgcggcaga ggctgaggcc gaggtgacgc   11760
tgcgggagct ccaggaagcc ctggaggagg aggtgctcac ccggcagagc ctgagccggg   11820
agatggaggc catccgcacg gacaaccaga acttcgccag gtcgggatcg gggccggggc   11880
cggggccggg atgcgggccg gtggcaaccc ttggcatccc ctctcgtccg gcccggacgg   11940
actcaccgtc cttacctccc cacagtcaac tacgcgaggc agaggctcgg aaccgggacc   12000
tagaggcaca cgtccggcag ttgcaggagc ggatggagtt gctgcaggca gagggagcca   12060
caggtgagtc cctcatgtgt ccccttcccc ggaggaccgg gaggaggtgg gccgtctgct   12120
ccgcggggcg tgtatagaca cctggaggag ggaagggacc cacgctgggg cacgccgcgc   12180
caccgccctc cttcgcccct ccacgcgccc tatgcctctt tcttctcctt ccagctgtca   12240
cgggggtccc cagtccccgg gccacggatc caccttccca tgtaagaccc ctctctttcc   12300
```

```
cctgcctcag acctgctgcc cattctgcag atcccctccc tggctcctgg tctcccegtc   12360 cagatatagg gctcacccta cgtctttgcg actttagagg gcagaagccc tttattcagc   12420
cccagatctc cctccgttca ggcctcacca gattccctcc gggatctccc tagataacct   12480
ccccaacctc gattcccctc gctgtctctc gccccaccgc tgagggctgg gctgggctcc   12540
gatcgggtca cctgtccctt ctctctccag ctagatggcc cccggccgt ggctgtgggc    12600 cagtgcccgc tggtggggcc aggcccatg caccgccgcc acctgctgct ccctgccagg    12660
gtacgtccgg ctgcccacgc cccctccgc cgtcgcgccc cgcgctccac ccgccccttg    12720
ccacccgctt agctgcgcat ttgcggggct gggcccacgg caggagggcg gatcttcggg   12780
cagccaatca acacaggccg ctaggaagca gccaatgacg agttcggacg ggattcgagg   12840
cgtgcgagtg gactaacaac agctgtaggc tgttggggcg ggggcgggc gcagggaaga    12900 gtgcgggccc acctatgggc gtaggcgggg cgagtcccag gagccaatca gaggcccatg   12960
ccgggtgttg acctcgccct ctcccgcag gtccctaggc ctggcctatc ggaggcgctt    13020
tccctgctcc tgttcgccgt tgttctgtct cgtgccgccg ccctgggctg cattgggttg   13080 gtggccacg ccggccaact caccgcagtc tggcgccgcc caggagccgc ccgcgctccc    13140
tgaaccctag aactgtcttc gactccgggg ccccgttgga agactgagtg cccggggcac   13200
ggcacagaag ccgcgcccac cgcctgccag ttcacaaccg ctccgagcgt gggtctccgc   13260
ccagctccag tcctgtgatc cgggcccgcc cctagcggc cggggaggga ggggccgggt    13320
ccgcggccgg cgaacggggc tcgaagggtc cttgtagccg ggaatgctgc tgctgctgct   13380
gctgctgctg ctgctgctgc tgctgctgct gctgctgctg ctgctggggg gatcacagac   13440
catttctttc tttcggccag gctgaggccc tgacgtggat gggcaaactg caggcctggg   13500
aaggcagcaa gccgggccgt ccgtgttcca tcctccacgc acccccacct atcgttggtt   13560
cgcaaagtgc aaagctttct tgtgcatgac gccctgctct ggggagcgtc tggcgcgatc   13620
tctgcctgct tactcgggaa atttgctttt gccaaaccg cttttttcggg gatcccgcgc    13680 ccccctcctc acttgcgctg ctctcggagc cccagccggc tccgcccgct tcggcggttt   13740
ggatatttat tgacctcgtc ctccgactcg ctgacaggct acaggacccc caacaacccc   13800
aatccacgtt ttggatgcac tgagacccg acattcctcg gtatttattg tctgtcccca    13860
cctaggaccc ccaccccga ccctcgcgaa taaaaggccc tccatctgcc caaagctctg    13920
gactccacag tgtccgcggt ttgcgttgtg ggccggaggc tccgcagcgg gccaatccgg   13980
aggcgtgtgg aggcggccga aggtctggga ggagctagcg ggatgcgaag cggccgaatc   14040
agggttgggg gaggaaaagc cacggggcgg ggctttggcg tccggccaat aggagggcga   14100
gcgggccacc cggaggcacc gccccgccc agctgtggcc cagctgtgcc accgagcgtc    14160
gagaagaggg ggctgggctg gcagcgcgcg cggccatcct ccttccactg cgcctgcgca   14220
cgccacgcgc atccgctcct gggacgcaag ctcgagaaaa gttgctgcaa actttctagc   14280
ccgttccccg ccctcctcc cggccagacc cgccccccct gcggagccgg gaattccgag    14340
gggcggagcg caggccgaga tggggaatgt gggggcctgc agaggaccct ggagacggag   14400
gcgtgcagaa g                                                        14411
```

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 2
acaataaata ccgagg                                                    16

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
tcaacaataa ataccgagg                                                 19

<210> SEQ ID NO 4
<211> LENGTH: 8
<212> TYPE: DNA
<213> ORGANISM: Artificial sequence
<220> FEATURE:
<223> OTHER INFORMATION: Synthetic oligonuclotide

<400> SEQUENCE: 4 cctcggta                                                              8

<210> SEQ ID NO 5
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 5 atttattgt                                                             9

<210> SEQ ID NO 6
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 6
ccucgguauu uauugu                                                    16

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucletide

<400> SEQUENCE: 7
ttgtgttcac aataaatacc gagg                                           24

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 8
acaataaatc cgagggttcc ctc                                            23

<210> SEQ ID NO 9
```

```
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
ggagccataa ataacacttg tgtt                                              24

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
cctcggtatt tattgt                                                       16

<210> SEQ ID NO 11
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 11
tcaccucggu auuuauugu                                                    19

<210> SEQ ID NO 12
<211> LENGTH: 16
<212> TYPE: RNA
<213> ORGANISM: Artificial sequence
<220> FEATURE:
<223> OTHER INFORMATION: Synthetic oligonucleotide.

<400> SEQUENCE: 12
ccucgguauu uauugu                                                       16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ctagttcact gaatgc                                                       16

<210> SEQ ID NO 14
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 14 gcattcag                                                                 8

<210> SEQ ID NO 15
<211> LENGTH: 9
<212> TYPE: DNA
<213> ORGANISM: Artificial sequence
<220> FEATURE:
<223> OTHER INFORMATION: Synthetic oligonucleotide

<400> SEQUENCE: 15
```

```
<210> SEQ ID NO 16
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 16 tgaactag                                                                  8

<210> SEQ ID NO 17
<211> LENGTH: 11
<212> TYPE: RNA
<213> ORGANISM: Artificial sequence
<220> FEATURE:
<223> OTHER INFORMATION: Synthetic oligonucleotide

<400> SEQUENCE: 17
cagugaacua g                                                             11

<210> SEQ ID NO 18
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 18
ctagttgcat                                                               10

<210> SEQ ID NO 19
<211> LENGTH: 10001
<212> TYPE: DNA
<213> ORGANISM: Mus musculus
<220> FEATURE:
<221> NAME/KEY: misc_feature
<222> LOCATION: (2)..(19)
<223> OTHER INFORMATION: bases at these positions are RNA

<400> SEQUENCE: 19
tgactatcag cctgtatggt cattaagttc tgtctaccct gggaaagcct ctgcccaaac       60
ctccctattc acaggtccta gaacgtagag gtggggagca ggacggtgcc gccaggccgt      120
gtgcgatcgc gagctctgga tctcaatgcg ccccggggcg ctgtttccca cgactccagc      180
agcttttcta aaaatccagg cagcctccag tttacgggat caacccgaga ctcgcttccc      240
tttgaaaatt ctagagtata aagtaaacgt acgagcaaag tatgtgtctt aacacttaat      300
ggatgacata gagaccaaaa aagccatgtc cgtgggccca gtaggccgca ataaggggcg      360
accaggaaac tgcagcacag ccccccgcag ccgccctgct cccacaccag tcattccagc      420
accgtggtga aggcgcttgg gggcggggcg gggcgcgcct cgcagcgag gctctgcagc       480 agaaactttg cctagaccgg ctggaaccgg ttagaaccgg tcgaaccgg ccggctgcca       540 gccctcgatt cagcagctca caaagggagg cggcgactca cgaccgcgt atccttgcgc       600 ctctccccac ccccttttgtc ctcgcgacgg gttccgcggt cctccccgcc ctccctggcg     660 cggccccccgc tttctgcgcc cagtgacgct ttctccatgg tcctgggaga aagagaaaaa    720 catccttttcc cctccgtcgt agttttagga agcgatgaga tagacctggg gaccttgcca    780
ccacgggccg ggctctgacg gttattagcg cagtgcgggt ggtgctcggc atggccgcca    840
```

```
aggtcgccgt gccctcacct gcagcgacca tggccttgct gggctgagac cgcagcctaa    900
catggcggac gtaggcaagc accaaagcgc tcgtgtaccc gggctcggaa aagtggcccc    960
gagagcagcc ggaggctgca ggtcgtccct acaggagcat tcccagtata aaccagtaca   1020
aagtgtcacc acctcagaag ccactcgcag ggccggtcac tttccgagag acctccatct   1080
tgtttcgcat gaaatggcag ccgctcgggg agttacaaaa tgggaagtgg aagctgaagc   1140
tgtgggaaag cctgttttaa cacttgcaac atacgctata ccctctgtcc tcccaggaaa   1200
acgcaaaagg tgttgaaaca tctgaaaaac ttggggctcc cattttttaat agctattagt   1260 tcatgttttt tctccttgtg accagaaatt ttaaacctat ttgtacctat ttagctggta   1320
caagctaaac atttctctgt attagcaagg tccaagaggc ccacacgacg tcaagaaaaa   1380
tctagaaact tggaagtcag gatctatttt taactctctg aggaactatt tttcttcctt   1440
caccaaggtg gtggagggtt actaggttcc ggtggagtga cgtgtcccott tgcaataaat   1500 accggcgctc cgggctctgc gtcaggcatt caggcagcga gagcagagca gcgtagagca   1560
gcacagctga gctcgtgagg caggagactc agcccgagga aatcgcagat aagttttttaa   1620 ttaaaaagat tgagcagtaa aaagaattag aactctaaac ttaagctaat agagtagctt   1680
atcgaaatat tacttagtct taataatcta agaagatctt aagagataac atgaaggctt   1740
atttaaacag tttgaaaaag gaaatgagga gaaagtatt tgtactgtat aatggaggct    1800
gaccagagca gtttaggaga ttgtaaaggg aggttttgtg aagttctaaa aggttctagt   1860
ttgaaggtcg gccttgtaga ttaaaacgaa ggttacctaa atagaatcta agtggcattt   1920
aaaacagtaa agttgtagag aatagtttga aaatgaggtg tagttttaaa agattgagaa   1980
aagtaggtta agttgacggc cgttataaaa atccttcgac tggcgcatgt acgtttgaag   2040
gcatgagttg gaaacaggga agatggaagt gttaggctag ccgggcgatg gtggcgcacg   2100
cctttaatcc tagcacttgg gaggcagagg caggcggatt tctgagttcg aggccagcct   2160
ggtctacaga gtgagttcca ggacagccag ggctacacag agaaaccctg tcttgaaaaa   2220
acaaaaaggt taggctagta tttggagaaa gaagattaga aaatggaagt gaaagacgaa   2280
gaagacatac aggaaggtga agaaaaaagct gttagagaag ataggaaaat agaagacaaa   2340
gcatctttag aagacagaaa aggtacttaa aggcacaggt agtaggaagc cgaagaatag   2400
aagatagaaa gaagcaagat agaaaaacaa aatggaagtt aagacaactt ggatgccag    2460 cattcaagat aggcaaagaa gataagattg aggccaaaag gttggataag atataaagtc   2520
agaaggaaat tatctttaaa gccataagtt caaatttctg atggagcgag cagtttagaa   2580
gagtctttag acagccacat acaagattga agctagcaat caaagctact aggactgaag   2640
taaaaagtta aggcagaatg cctttgaaga gttagaagaa tattaaaagc cttaacttgt   2700
agcttaattt tgcttgatga caaaaggact tttgataaca gtttcaagat tgtcagcatt   2760
ttgcattgga cttgagctga ggtgcttttta aaatcctaac gactagcatt ggcagctgac   2820
ccaggtctac acagaagtgc attcagtgaa ctaggaagac aggagcggca gacaggagtc   2880
ccgaagccag tttggtgaag ctaggaagga ctgaggagcc agcagcagca gtgcatggtg   2940
aagatagccc aggaaagagt gcggttcggt ggaggaagct aggaagaagg agccatacgg   3000
atgtggtggt gaagctggga aagggttcca ggatggtgga gcgagagcga gttggtgatg   3060
aagctagctg gcggcttggc ttgtcaactg cgcggaggag gcgagcaggc attgtggaga   3120
ggatagatag cggctcctag accagcatgc cagtgtgcaa gaaaggctgc agggagagca   3180
tgcggtgcgg taacattcct tgaggtcggc aacatggtgg tggttttctg taacttggat   3240
```

```
ggtaacttgt ttactttgtc ttaatagtta tgggggagtt gtaggcttct gtgtaaagag    3300
atatatctgg ggctgtatgt aggcctttgc gggtgttgta ggttttctt tttcagggtt     3360
atgtcctctt gcatcttgtc agaagctttt gagggctgac tgccaaggcc cagaaagaag    3420
aatggtagat ggcaagttgt ctttaaccgc tcagagggga atgaatggta gagccagcac    3480
aacctcccag ttttgtaaga cgttgtagtt tgaacagatg acctaccaca agcctcactc    3540
ctgtgtaggg gaggtaattg ggcaaagtgc ttttggggga atgggggcaa aatatatttt    3600
gagttctttt cccttaggt ctgtctagaa tcctaaaggc agatgactca agggaaccag      3660
aaaaaaggaa atccactctc aggataagca gagctcgcca ggtttacagt ttgtaggaag    3720
tagaggatgg atgctagctt tcacactgag tgtggaggag ctggccatgg cggaattgct    3780
ggtagtttac tctttccccc tcccttaatg agatttgtaa aatcctaaac acttttactt    3840
gaaatatttg ggagtggtct taacagggag gagtgggtgg gggaaacgtt ttttttctaa    3900
gattttccac agatgctata gttgtgttga cacactgggt tagagaaggc gtgtactgct    3960
atgctgttgg cacgacacct tcagggactg gagctgcctt ttgtccttgg aagagttttc    4020
ccagttgccg ctgaagtcag cacagtgcgg ctttggttca cagtcacctc aggagaacct    4080
caggagcttg gctaggccag aggttgaagt taagttttac agcaccgtga tttaaaatat    4140
ttcattaaag gggaggggta aaacttagtt ggctgtggcc ttgtgtttgg gtgggtgggg    4200
gtgttaggta attgtttagt ttatgatttc agataatcat accagagaac ttaaatattt    4260
ggaaaaacag gaaatctcag ctttcaagtt ggcaagtaac tcccaatcca gttttgctt    4320
cttttttcct ttttcttttt ttgaggcggg cagctaagga aggttggttc ctctgccggt    4380
ccctcgaaag cgtagggctt gggggttggt ctggtccact gggatgatgt gatgctacag    4440
tggggactct tctgaagctg ttggatgaat atagattgta gtgtgtggtt ctcttttgaa    4500
attttttca ggtgacttaa tgtatcttaa taactactat aggaacaaag gaagtggctt      4560
taatgaccct gaaggaattt cttctggtga tagcttttat attatcaagt aagagatact    4620
atctcagttt tgtataagca agtcttttc ctagtgtagg agaaatgatt ttccttgtga      4680
ctaaacaaga tgtaaaggta tgcttttttt cttcttgtgc attgtatact tgtgtttatt    4740
tgtaacttat aatttaagaa ttatgataat tcagcctgaa tgtcttttag agggtgggct    4800
tttgttgatg agggagggga aacctttttt tttctgtaga ccttttttcag ataacaccat   4860
ctgagtcata accagcctgg cagtgtgatg acgtagatgc agagggagca gctccttggt    4920
gaatgagtga taagtaaagg cagaaaaaat aatgtcatgt ctccatgggg aatgagcatg    4980
agccagagat tgttcctact gatgaaaagc tgcatatgca aaaatttaag caaatgaaag    5040
caaccagtat aaagttatgg caatacccttt aaaagttatg gcttatctac caagctttat   5100
ccacaaaagt aaagaattga tgaaaaacag tgaagatcaa atgttcatct caaaactgct    5160
tttacaaaag cagaatagaa atgaagtgaa aatgctgcat taagcctgga gtaaaaagaa    5220
gctgagcttg ttgagatgag tgggatcgag cggctgcgag gcggtgcagt gtgccaatgt    5280
ttcgtttgcc tcagacaggt ttctcttcat aagcagaaga gttgcttcat tccatctcgg    5340
agcaggaaac agcagactgc tgttgacaga taagtgtaac ttggatctgc agtattgcat    5400
gttagggata gataagtgcc ttttttctct ttttccaaaa agacctgtag agctgttgaa    5460
tgtttgcagc tggcccctct taggcagttc agaattttga gtagttttcc catccagcct    5520
cttaaaaatt cctaagcctt gcaccgatgg gctttcatga tgggatagct aataggcttt    5580
```

```
tgcatcgtaa acttcaacac aaaagcctac atgattaatg cctactttaa ttacattgct    5640
tacaagatta aggaatcttt atcttgaaga ccccatgaaa gggatcatta tgtgctgaaa    5700
attagatgtt catattgcta aaatttaaat gtgctccaat gtacttgtgc ttaaaatcat    5760
taaattatac aaattaataa aatacttcac tagagaatgt atgtatttag aaggctgtct    5820
ccttatttaa ataaagtctt gtttgttgtc tgtagttagt gtgggcaatt ttgggggggat   5880 gttcttctct aatcttttca gaaacttgac ttcgaacact taagtggacc agatcaggat    5940
ttgagccaga agaccgaaat taactttaag gcaggaaaga caaattttat tctccatgca   6000
gtgatgagca tttaataatt gcaggcctgg catagaggcc gtctaactaa ggactaagta    6060
ccttaggcag gtgggagatg atggtcagag taaaggtaa ctacatattt tgtttccaga    6120
aagtcagggg tctaatttga ccatggctaa acatctaggg taagacactt tcccccaca    6180 tttccaaata tgcatgttga gtttaaatgc ttacgatcat ctcatccact ttagcctttt    6240
gtcacctcac ttgagccacg agtggggtca ggcatgtggg tttaaagagt tttcctttgc    6300
agagcctcat ttcatccttc atggagctgc tcaggacttt gcatataagc gcttgcctct    6360
gtcttctgtt ctgctagtga gtgtgtgatg tgagaccttg cagtgagttt gttttttcctg   6420 gaatgtggag ggaggggggg atggggctta cttgttctag ctttttttttt acagaccaca    6480 cagaatgcag gtgtcttgac ttcaggtcat gtctgttctt tggcaagtaa tatgtgcagt    6540
actgttccaa tctgctgcta ttagaatgca ttgtgacgcg actggagtat gattaaagaa    6600
agttgtgttt ccccaagtgt ttggagtagt ggttgttgga ggaaaagcca tgagtaacag    6660
gctgagtgtt gaggaaatgg ctctctgcag ctttaagtaa cccgtgtttg tgattggagc    6720
cgagtccctt tgctgtgctg ccttaggtaa atgtttttgt tcatttctgg tgagggggt     6780 tgggagcact gaagccttta gtctcttcca gattcaactt aaaatctgac aagaaataaa    6840
tcagacaagc aacattcttg aagaaatttt aactggcaag tggaaatgtt ttgaacagtt    6900
ccgtggtctt tagtgcatta tctttgtgta ggtgttctct ctcccctccc ttggtcttaa    6960
ttcttacatg caggaacatt gacaacagca gacatctatc tattcaaggg gccagagaat    7020
ccagacccag taaggaaaaa tagcccattt actttaaatc gataagtgaa gcagacatgc    7080
cattttcagt gtggggattg ggaagcccta gttctttcag atgtacttca gactgtagaa    7140
ggagcttcca gttgaattga aattcaccag tggacaaaat gaggacaaca ggtgaacgag    7200
ccttttcttg tttaagatta gctactggta atctagtgtt gaatcctctc cagcttcatg    7260
ctggagcagc tagcatgtga tgtaatgttg gccttgggt ggaggggtga ggtgggcgct     7320 aagcctttt ttaagatttt tcaggtaccc ctcactaaag gcactgaagg cttaatgtag     7380
gacagcggag ccttcctgtg tggcaagaat caagcaagca gtattgtatc gagaccaaag    7440
tggtatcatg gtcggttttg attagcagtg gggactaccc taccgtaaca ccttgttgga    7500
attgaagcat ccaaagaaaa tacttgagag gccctgggct tgttttaaca tctgaaaaaa    7560
aggctgtttt tatagcagcg gttaccagcc caaacctcaa gttgtgcttg caggggaggg    7620
aaaaggggga aagcgggcaa ccagtttccc cagcttttcc agaatcctgt tacaaggtct    7680
ccccacaagt gatttctctg ccacatcgcc accatgggcc tttggcctaa tcacagaccc    7740 ttcaccccctc accttgatgc agccagtagc tggatccttg aggtcacgtt gcatatcggt    7800
ttcaaggtaa ccatggtgcc aaggtcctgt gggttgcacc agaaaaggcc atcaattttc    7860
cccttgcctg taatttaaca ttaaaaccat agctaagatg ttttatacat agcacctatg    7920
cagagtaaac aaaccagtat gggtatagta tgtttgatac cagtgctggg tgggaatgta    7980
```

```
ggaagtcgga tgaaaagcaa gcctttgtag gaagttgttg gggtgggatt gcaaaaattc    8040
tctgctaaga cttttcagg tggacataac agacttggcc aagctagcat cttagtggaa    8100
gcagattcgt cagtagggtt gtaaaggttt ttcttttcct gagaaaacaa cctttgttt    8160 tctcaggttt tgcttttgg cctttcccta gctttaaaaa aaaaaaagca aaagacgctg    8220
gtggctggca ctcctggttt ccaggacggg gttcaagtcc ctgcggtgtc tttgcttgac    8280
tcttatatca tgaggccatt acatttttct tggagggttc taaaggctct gggtatggta    8340
gctgatatca ctggaacact ccccagcctc agtgttgaac tcttgataat taactgcatt    8400
gtctttcagg ttatgcccaa ttcgtcttat tacctctgag tcgacacacc tcctactatt    8460
tattgaatac tttgatttta tgaaataaaa actaaatatc tctcattgtg tgcttctttg    8520
tgcataaaac acaggcttat tttaagccta aagagaccaa atgtctgatc tacctcagct    8580
tctccgatta gtgaggcctt ccctgtttcc ttgggctgca tggctctttc atgcagatgg    8640
ctctaaagtt gggcttgggt cctaggtggc cactcttgca cctcaggaac acaaggcctt    8700
tccctgctgt tcaggctctc ctccctgaga aaacattctg gattgtctat gaggaagttg    8760
ggaaaagatg gtgtcgaaaa gaggtggtgt gcattgctcc tctgttccta acactggatg    8820
gaagactagt tttcatgtag tttagggaaa tagttataca tggtctaaag gcccaaaaac    8880
attcccagag tgtatgcaat actgtgtgta agtgtgcact gcgtgtgttt ggaggtcaga    8940
acttctctga ggttctagag atgaagcaag tcctcagcca tggcccaaga atgggaagga    9000
actgggtcct gctgtaccac ttcccattcc ttaaggaaca gttggcccg gtgtggtgca     9060 agcatggtcg gtcactgaaa aaagaaaacc cacttaggtt tcacaggctt gaagagctgc    9120
atgtcatcca gcaaattact ggctgctgta aggacaggcc cctaggtccc agtcccaggt    9180
gcccttcctg ccactcaatc aagccttaca ccctgggcaa aaacatcctg cgttgaaggt    9240
tcagctccca gggctggaaa cttgtgctgg catctacccc agttcaaagg gctcagcac    9300 attgacaact aaaactaagc cctcaggtga gcaaatggt ctccttaagg caatcatggt     9360
cattggtgtt cctgcagtaa aggacagcat cacagctgat gtctgtgtac tggctagttt    9420
tgtatcaact tgacacagct ggaattatca cagagaaagc ttcagttggg gaagtgcctc    9480
caagagatcc tccacgagat cctgctctaa ggcattttct caattagtga tcaaggggga    9540
aagacccctt gtgtgtggga ccatctctgg gctggtagtc ttggttcagt tctataagag    9600
agcaggctga gcaagccagg ggaagcaagc cagtaaagaa catccctcca tggcctctgc    9660
atcagctcct gcttcctgac ctgcttgagt tccagtcctg acttccttgg tgatgaacag    9720
cagtatggaa gtgtaagccg aataaaccct gtcctcccca acttgcttct tggtcatgtt    9780
tgtgcaggaa tagaaaccct gactaagaca gtctgagacc tgacagatct gtgctaaagt    9840
ctggtaccaa ctgagctaga ccctgccaca cacctcagta atggcccatt ctgaattcac    9900
ccagagctga ggctttgccg aggtgaggca caaagacttc actggagagc aggagatatg    9960
aacagaggtt ggggctcaca cttcctgatt gggggccagg a                        10001
```

CONJUGATED ANTISENSE COMPOUNDS AND THEIR USE

SEQUENCE LISTING

The present application is being filed along with a Sequence Listing in electronic format. The Sequence Listing is provided as a file entitled CORE0145USASEQ_ST25.txt, created on Jun. 10, 2020, which is 24 Kb in size. The information in the electronic format of the sequence listing is incorporated herein by reference in its entirety.

BACKGROUND

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. For another example, an antisense oligonucleotide targeting ApoB, KYNAMRO™, has been approved by the U.S. Food and Drug Administration (FDA) as an adjunct treatment to lipid-lowering medications and diet to reduce low density lipoprotein-cholesterol (LDL-C), ApoB, total cholesterol (TC), and non-high density lipoprotein-cholesterol (non HDL-C) in patients with homozygous familial hypercholesterolemia (HoFH).

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy. Traditionally, antisense compounds, including modified oligonucleotides, have demonstrated good functional uptake into liver tissue. However, there is still a need to facilitate uptake and distribution of antisense compounds into other cell types, such as CNS tissue or muscle tissue.

SUMMARY OF THE INVENTION

Oligomeric compounds typically show good distribution to the liver after administration to a subject. However, in certain embodiments, a need exists to deliver oligomeric compounds to other tissues within a subject. For example, a need exists to deliver oligomeric compounds to one or more extra-hepatic tissues, such as CNS tissue or muscle tissue. A need also exists to deliver oligomeric compounds systemically and modulate a CNS target, e.g. the systemically delivered oligomeric compound crosses the blood-brain barrier and modulates a nucleic acid target in the CNS.

The present disclosure provides half duplex oligomeric compounds. Half duplex oligomeric compounds have a first modified oligonucleotide and a second modified oligonucleotide, wherein the first modified oligonucleotide is 14-30 linked nucleosides and has a nucleobase sequence complementary to the nucleobase sequence of the second oligomeric compound and to a nucleic acid target, and wherein the second modified oligonucleotide has between 6-12 linked nucleosides. In certain embodiments, these half duplex oligomeric compounds have one or more improved properties compared to either the first modified oligonucleotide or second modified oligonucleotide alone. One type of improved property is an improved safety profile. For example, a half duplex may have much better tolerability than either the first modified oligonucleotide or second modified oligonucleotide alone. Another type of improved property is improved uptake in a particular cell type. In certain embodiments, the half duplex enhances uptake and/or activity in muscle tissues. In certain embodiments, the half duplex enhances uptake and/or activity in the CNS. In certain embodiments, the half duplex can penetrate the blood brain barrier to a greater extent than the single-stranded version of either the first modified oligonucleotide or the second modified oligonucleotide alone. In certain embodiments, a systemically administered half duplex can penetrate the blood brain barrier to a greater extent than the single-stranded version of either the first modified oligonucleotide or the second modified oligonucleotide alone. In certain embodiments, a systemically administered half duplex can modulate a target nucleic acid in CNS tissue. In certain embodiments, the tissue is the striatum. In certain embodiments, the tissue is the spinal cord. In certain embodiments, the tissue is the cerebellum. In certain embodiments, the tissue is the cortex.

In certain embodiments, the second modified oligonucleotide of the half duplex comprises a conjugate group. In certain embodiments, the conjugate group enhances uptake and/or activity in an extra hepatic tissue. In certain embodiments, the conjugate group enhances uptake and/or activity in muscle tissue or CNS tissue.

In certain embodiments, the present disclosure provides methods of modulating the amount or activity of a target nucleic acid in an extra-hepatic tissue and/or extra-hepatic cell type by contacting the cell with a half duplex. In certain such embodiments, the present disclosure provides methods of treating diseases in which modulating the amount or activity of the target nucleic acid in the liver is not sufficient to provide a therapeutic benefit. For example, the present disclosure provides methods of modulating the amount or activity of the target nucleic acid in the CNS. The present disclosure also provides methods of modulating the amount or activity of the target nucleic acid in muscle tissue.

The present disclosure provides the following non-limiting embodiments:

Embodiment 1. A compound comprising a first oligomeric compound and a second oligomeric compound, wherein the first oligomeric compound comprises a first modified oligonucleotide consisting of 14-30 linked nucleosides and has a nucleobase sequence complementary to the nucleobase sequence of the second oligomeric compound and to a nucleic acid target; and the second oligomeric compound comprises a second modified oligonucleotide consisting of 6-12 linked nucleosides.

Embodiment 2. The compound of embodiment 1, wherein the first modified oligonucleotide has a nucleobase sequence that is at least 80% complementary to the nucleobase sequence of the target nucleic acid, when measured across the entire nucleobase sequence of the first modified oligonucleotide.

Embodiment 3. The compound of embodiment 1, wherein the first modified oligonucleotide has a nucleobase sequence that is at least 90% complementary to the nucleobase sequence of the target nucleic acid, when measured across the entire nucleobase sequence of the first modified oligonucleotide.

Embodiment 4. The compound of embodiment 1, wherein the first modified oligonucleotide has a nucleobase sequence that is 100% complementary to the nucleobase sequence of the target nucleic acid, when measured across the entire nucleobase sequence of the first modified oligonucleotide.

Embodiment 5. The compound of any of embodiments 1-4, wherein the first modified oligonucleotide has at least 8 contiguous nucleobases of SEQ ID NO: 2.

Embodiment 6. The compound of any of embodiments 1-4, wherein the first modified oligonucleotide has at least 9 contiguous nucleobases of SEQ ID NO: 2.

Embodiment 7. The compound of any of embodiments 1-4, wherein the first modified oligonucleotide has at least 10 contiguous nucleobases of SEQ ID NO: 2.

Embodiment 8. The compound of any of embodiments 1-4, wherein the first modified oligonucleotide has at least 11 contiguous nucleobases of SEQ ID NO: 2.

Embodiment 9. The compound of any of embodiments 1-4, wherein the first modified oligonucleotide has at least 12 contiguous nucleobases of SEQ ID NO: 2.

Embodiment 10. The compound of any of embodiments 1-9, wherein the first modified oligonucleotide comprises at least one modified nucleoside.

Embodiment 11. The compound of embodiment 10, wherein the first modified oligonucleotide comprises at least one modified nucleoside comprising a modified sugar moiety.

Embodiment 12. The compound of embodiment 11, wherein the first modified oligonucleotide comprises at least one modified nucleoside comprising a bicyclic sugar moiety.

Embodiment 13. The compound of embodiment 12, wherein the first modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 14. The compound of embodiment 12, wherein the first modified oligonucleotide comprises at least one modified nucleoside comprising a bicyclic sugar moiety selected from among cEt or LNA.

Embodiment 15. The compound of embodiment 12, wherein the first modified oligonucleotide comprises at least one modified nucleoside comprising a cEt bicyclic sugar moiety.

Embodiment 16. The compound of any of embodiments 10-15, wherein the first modified oligonucleotide comprises at least one modified nucleoside comprising a modified non-bicylcic sugar moiety.

Embodiment 17. The compound of embodiment 16, wherein the first modified oligonucleotide comprises at least one modified nucleoside comprising a non-bicyclic sugar moiety comprising a 2'-MOE or 2'-OMe.

Embodiment 18. The compound of embodiment 16, wherein the first modified oligonucleotide comprises at least one modified nucleoside comprising a 2'-MOE modified nucleoside.

Embodiment 19. The compound of any of embodiments 10-18, wherein the first modified oligonucleotide comprises at least one modified nucleoside comprising a sugar surrogate.

Embodiment 20. The compound of embodiment 19, wherein the first modified oligonucleotide comprises at least one modified nucleoside comprising a sugar surrogate selected from a morpholino, a PNA, a F-HNA, a THP, or a modified THP.

Embodiment 21. The compound of any of embodiments 1-20, wherein the first modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-nucleosides; wherein
each of the 5'-region nucleosides and each of the 3'-region comprises a modified sugar moiety and each of the central region nucleosides comprises an unmodified DNA sugar moiety.

Embodiment 22. The compound of any of embodiments 1-20, wherein the first modified oligonucleotide has a sugar motif comprising:
a 5'-region consisting of 5 linked 5'-nucleosides;
a central region consisting of 10 linked central region nucleosides; and
a 3'-region consisting of 5 linked 3'-nucleosides; wherein
each of the 5'-region nucleosides and each of the 3'-region comprises a modified sugar moiety and each of the central region nucleosides comprises an unmodified DNA sugar moiety.

Embodiment 23. The compound of any of embodiments 1-20, wherein the first modified oligonucleotide has a sugar motif comprising:
a 5'-region consisting of 3 linked 5'-nucleosides;
a central region consisting of 10 linked central region nucleosides; and
a 3'-region consisting of 3 linked 3'-nucleosides; wherein
each of the 5'-region nucleosides and each of the 3'-region comprises a modified sugar moiety and each of the central region nucleosides comprises an unmodified DNA sugar moiety.

Embodiment 24. The compound of any of embodiments 1-11 or 16-18, wherein each nucleoside of the first modified oligonucleotide comprises a non-bicyclic sugar moiety comprising a 2'-MOE.

Embodiment 25. The compound of any of embodiments 1-11 or 16-18, wherein each nucleoside of the first modified oligonucleotide comprises a non-bicyclic sugar moiety comprising a 2'-OMe.

Embodiment 26. The compound of any of embodiments 1-11 or 16-20, wherein each nucleoside of the first modified oligonucleotide comprises a sugar surrogate selected from a morpholino, a PNA, a F-HNA, a THP, or a modified THP.

Embodiment 27. The compound of any of embodiments 1-20 or 24-26, wherein the first modified oligonucleotide consists of 14-22 linked nucleosides.

Embodiment 28. The compound of any of embodiments 1-20 or 24-26, wherein the first modified oligonucleotide consists of 14-20 linked nucleosides.

Embodiment 29. The compound of any of embodiments 1-20 or 24-26, wherein the first modified oligonucleotide consists of 16-20 linked nucleosides.

Embodiment 30. The compound of any of embodiments 1-20 or 24-26, wherein the first modified oligonucleotide consists of 16-18 linked nucleosides.

Embodiment 31. The compound of any of embodiments 1-20 or 24-26, wherein the first modified oligonucleotide consists of 16 linked nucleosides.

Embodiment 32. The compound of any of embodiments 1-22 or 24-26, wherein the first modified oligonucleotide consists of 20 linked nucleosides.

Embodiment 33. The compound of any of embodiments 1-32, wherein the first modified oligonucleotide comprises at least one modified internucleoside linkage.

Embodiment 34. The compound of embodiment 33, wherein each internucleoside linkage of the first modified oligonucleotide is a modified internucleoside linkage.

Embodiment 35. The compound of embodiment 33 or 34 wherein at least one internucleoside linkage of the first oligonucleotide is a phosphorothioate internucleoside linkage.

Embodiment 36. The compound of any of embodiments 1-33 wherein the first modified oligonucleotide comprises at least one unmodified phosphodiester internucleoside linkage.

Embodiment 37. The compound of any of embodiments 1-36, wherein each internucleoside linkage of the first oligonucleotide is either an unmodified phosphodiester internucleoside linkage or a phosphorothioate internucleoside linkage.

Embodiment 38. The compound of embodiment 34, wherein each internucleoside linkage of the first oligonucleotide is a phosphorothioate internucleoside linkage.

Embodiment 39. The compound of embodiments 1-38, wherein the second modified oligonucleotide is at least 75% complementary to the first modified oligonucleotide, over the length of the second modified nucleotide.

Embodiment 40. The compound of embodiments 1-38, wherein the second modified oligonucleotide is at least 80% complementary to the first modified oligonucleotide, over the length of the second modified nucleotide.

Embodiment 41. The compound of embodiments 1-38, wherein the second modified oligonucleotide is at least 90% complementary to the first modified oligonucleotide, over the length of the second modified nucleotide.

Embodiment 42. The compound of embodiments 1-38, wherein the second modified oligonucleotide is at least 100% complementary to the first modified oligonucleotide, over the length of the second modified nucleotide.

Embodiment 43. The compound of any of embodiments 42, wherein the second modified oligonucleotide has at least 6 contiguous nucleobases of SEQ ID NO: 4.

Embodiment 44. The compound of any of embodiments 42, wherein the second modified oligonucleotide has at least 6 contiguous nucleobases of SEQ ID NO: 5.

Embodiment 45. The compound of any of embodiments 1-44, wherein the second modified oligonucleotide comprises at least one modified nucleoside.

Embodiment 46. The compound of embodiment 45, wherein the second modified oligonucleotide comprises at least one modified nucleoside comprising a modified sugar moiety.

Embodiment 47. The compound of embodiment 46, wherein the second modified oligonucleotide comprises at least one modified nucleoside comprising a bicyclic sugar moiety.

Embodiment 48. The compound of embodiment 47, wherein the second modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 49. The compound of embodiment 48, wherein the second modified oligonucleotide comprises at least one modified nucleoside comprising a bicyclic sugar moiety selected from among cEt or LNA.

Embodiment 50. The compound of embodiment 48, wherein the second modified oligonucleotide comprises at least one modified nucleoside comprising a cEt bicyclic sugar moiety.

Embodiment 51. The compound of any of embodiments 45-50, wherein the second modified oligonucleotide comprises at least one modified nucleoside comprising a modified non-bicylcic sugar moiety.

Embodiment 52. The compound of embodiment 51, wherein the second modified oligonucleotide comprises at least one modified nucleoside comprising a non-bicyclic sugar moiety comprising a 2'-MOE or 2'-OMe.

Embodiment 53. The compound of any of embodiments 1-52, wherein the second modified oligonucleotide comprises at least one modified nucleoside comprising a sugar surrogate.

Embodiment 54. The compound of embodiment 53, wherein the second modified oligonucleotide com- Embodiment 55. The compound of any of embodiments 1-54, wherein the second modified oligonucleotide has a sugar motif comprising:
a 5'-region consisting of 2-4 linked 5'-nucleosides;
a central region consisting of 2-4 linked central region nucleosides; and
a 3'-region consisting of 2-4 linked 3'-nucleosides; wherein
each of the 5'-region nucleosides and each of the 3'-region comprises a modified sugar moiety and each of the central region nucleosides comprises an unmodified DNA sugar moiety.

Embodiment 56. The compound of any of embodiments 1-54, wherein the second modified oligonucleotide has a sugar motif comprising:
a 5'-region consisting of 2 linked 5'-nucleosides;
a central region consisting of 4 linked central region nucleosides; and
a 3'-region consisting of 2 linked 3'-nucleosides; wherein
each of the 5'-region nucleosides and each of the 3'-region comprises a modified sugar moiety and each of the central region nucleosides comprises an unmodified DNA sugar moiety.

Embodiment 57. The compound of any of embodiments 1-54, wherein the second modified oligonucleotide has a sugar motif comprising:
a 5'-region consisting of 4 linked 5'-nucleosides;
a central region consisting of 2 linked central region nucleosides; and
a 3'-region consisting of 3 linked 3'-nucleosides; wherein
each of the 5'-region nucleosides and each of the 3'-region comprises a modified sugar moiety and each of the central region nucleosides comprises an unmodified DNA sugar moiety.

Embodiment 58. The compound of embodiments 1-38 or embodiments 51-57 wherein each nucleoside of the second modified oligonucleotide comprises a non-bicyclic sugar moiety comprising a 2'-MOE.

Embodiment 59. The compound of embodiments 1-38 or embodiments 51-57 wherein each nucleoside of the second modified oligonucleotide comprises a non-bicyclic sugar moiety comprising a 2'-OMe.

Embodiment 60. The compound of any of embodiments 1-38 or embodiments 51-57, wherein each nucleoside of the second modified oligonucleotide comprises a sugar surrogate selected from a morpholino, a PNA, a F-HNA, a THP, or a modified THP.

Embodiment 61. The compound of any of embodiments 1-60, wherein the second modified oligonucleotide consists of 6-10 linked nucleosides.

Embodiment 62. The compound of any of embodiments 1-60, wherein the second modified oligonucleotide consists of 7-10 linked nucleosides.

Embodiment 63. The compound of any of embodiments 1-60, wherein the second modified oligonucleotide consists of 8-10 linked nucleosides.

Embodiment 64. The compound of any of embodiments 1-60, wherein the second modified oligonucleotide consists of 8-9 linked nucleosides.

Embodiment 65. The compound of any of embodiments 1-60, wherein the second modified oligonucleotide consists of 7-9 linked nucleosides.

Embodiment 66. The compound of any of embodiments 1-56, wherein the second modified oligonucleotide consists of 8 linked nucleosides.

Embodiment 67. The compound of any of embodiments 1-55 or 57, wherein the second modified oligonucleotide consists of 9 linked nucleosides.

Embodiment 68. The compound of any of embodiments 1-67, wherein the second modified oligonucleotide comprises at least one modified internucleoside linkage.

Embodiment 69. The compound of embodiment 68, wherein each internucleoside linkage of the second modified oligonucleotide is either an unmodified phosphodiester internucleoside linkage or a phosphorothioate internucleoside linkage.

Embodiment 70. The compound of embodiment 68 or 69, wherein each nucleoside linkage of the second modified oligonucleotide is a phosphorothioate internucleoside linkage.

Embodiment 71. The compound of embodiment 69, wherein each nucleoside linkage of the second modified oligonucleotide is an unmodified phosphodiester internucleoside linkage.

Embodiment 72. The compound of any of embodiments 1-71, wherein the first modified oligonucleotide or the second modified oligonucleotide comprises at least one modified nucleobase.

Embodiment 73. The compound of embodiment 72, wherein the modified nucleobase is a 5'-Me cytosine.

Embodiment 74. The compound of embodiment 72, wherein each nucleobase of each modified oligonucleotide is either an unmodified nucleobase or is 5'-Me cytosine.

Embodiment 75. The compound of any of embodiments 1-74, wherein the 3'-most nucleobase of the second modified oligonucleotide is complementary to the 5'-most nucleobase of the first modified oligonucleotide.

Embodiment 76. The compound of any of embodiments 1-75, wherein the conjugate group is covalently attached to the first modified oligonucleotide.

Embodiment 77. The compound of any of embodiments 1-75, wherein the conjugate group is covalently attached to the second modified oligonucleotide.

Embodiment 78. The compound of any of embodiments 1-75, wherein the conjugate group is covalently attached to the 3'-end of the first modified oligonucleotide.

Embodiment 79. The compound of any of embodiments 1-75, wherein the conjugate group is covalently attached to the 5'-end of the first modified oligonucleotide.

Embodiment 80. The compound of any of embodiments 1-75, wherein the conjugate group is covalently attached to the 3'-end of the second modified oligonucleotide.

Embodiment 81. The compound of any of embodiments 1-75, wherein the conjugate group is covalently attached to the 5'-end of the second modified oligonucleotide.

Embodiment 82. The compound of any of embodiments 1-81, wherein the conjugate group comprises a conjugate linker.

Embodiment 83. The compound of any of embodiments 1-82, wherein the conjugate group comprises a conjugate moiety.

Embodiment 84. The compound of any of embodiments 1-83, wherein the conjugate group consists of a conjugate linker and a conjugate moiety.

Embodiment 85. The compound of any of embodiments 1-84, wherein the conjugate moiety is a lipid.

Embodiment 86. The compound of any of embodiments 1-84, wherein the conjugate moiety is cholesterol.

Embodiment 87. The compound of any of embodiments 78-86, wherein the conjugate linker is TCA.

Embodiment 88. The compound of any of embodiments 78-86, wherein the conjugate linker is TEG.

Embodiment 89. The compound of any of embodiments 78-86, wherein the conjugate linker is hexylamino.

Embodiment 90. The compound of any of embodiments 1-89, where the compound exists primarily as a duplex at or below 57° C.

Embodiment 91. The compound of any of embodiments 1-89, where the compound exists primarily as a duplex at or below 47° C.

Embodiment 92. The compound of any of embodiments 1-89, where the compound exists primarily as a duplex at 37° C.

Embodiment 93. A pharmaceutical composition comprising the compound of any embodiments 1-92 and a pharmaceutically acceptable carrier or diluent.

Embodiment 94. A pharmaceutical composition comprising the compound of any of embodiments 1-92 and a pharmaceutically acceptable carrier or diluent.

Embodiment 95. A method comprising administering to an animal the compound or pharmaceutical composition of any of embodiments 1-94.

Embodiment 96. The method of embodiment 95, wherein the compound or pharmaceutical composition of any of embodiments 1-94 is administered systemically.

Embodiment 97. A method of treating a disease associated with an extra-hepatic nucleic acid target comprising administering to an individual having or at risk for developing a disease associated with the extra-hepatic nucleic acid target a therapeutically effective amount of the compound or pharmaceutical composition of any of embodiments 1-94; and thereby treating the disease associated with the extra-hepatic nucleic acid target.

Embodiment 98. The method of embodiment 97, wherein the extra-hepatic nucleic acid target is a muscle target.

Embodiment 99. The method of embodiment 97, wherein the extra-hepatic nucleic acid target is DMPK.

Embodiment 100. The method of embodiment 97, wherein the extra-hepatic nucleic acid target is a CNS target.

Embodiment 101. The method of any of embodiments 97-100, wherein the administration is systemic.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"Antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the antisense compound.

"Antisense compound" means a compound comprising an antisense oligonucleotide and optionally one or more additional features, such as a conjugate group or terminal group.

"Antisense oligonucleotide" means an oligonucleotide that (1) has a nucleobase sequence that is at least partially complementary to a target nucleic acid and that (2) is capable of producing an antisense activity in a cell or animal.

"Ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

"Bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"Cleavable moiety" means a bond or group of atoms that is cleaved under physiological conditions, for example, inside a cell, an animal, or a human.

"Complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Extra-hepatic cell type" means a cell type that is not a hepatocyte.

"Extra-hepatic nucleic acid target" means a target nucleic acid that is expressed in tissues other than liver. In certain embodiments, extra-hepatic nucleic acid targets are not expressed in the liver or not expressed in the liver at a significant level. In certain embodiments, extra-hepatic nucleic acid targets are expressed outside the liver and also in the liver.

"Extra-hepatic tissue" means a tissue other than liver.

"Fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

"Gapmer" means an antisense oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"Linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

"Lipophilic group" or "lipophilic" in reference to a chemical group means a group of atoms that is more soluble in lipids or organic solvents than in water and/or has a higher affinity for lipids than for water. In certain embodiments, lipophilic groups comprise a lipid. As used herein "lipid" means a molecule that is not soluble in water or is less soluble in water than in organic solvents. In certain embodiments, compounds of the present invention comprise lipids selected from saturated or unsaturated fatty acids, steroids, fat soluble vitamins, phospholipids, sphingolipids, hydrocarbons, mono-, di-, and tri-glycerides, and synthetic derivatives thereof.

"Non-bicyclic modified sugar" or "non-bicyclic modified sugar moiety" means a modified sugar moiety that comprises a modification, such as a substitutent, that does not form a bridge between two atoms of the sugar to form a second ring.

"Linked nucleosides" are nucleosides that are connected in a continuous sequence (i.e. no additional nucleosides are present between those that are linked).

"Mismatch" or "non-complementary" means a nucleobase of a first oligonucleotide that is not complementary with the corresponding nucleobase of a second oligonucleotide or target nucleic acid when the first and second oligomeric compound are aligned.

"MOE" means methoxyethyl. "2'-MOE" means a —OCH$_2$CH$_2$OCH$_3$ group at the 2' position of a furanosyl ring.

"Motif" means the pattern of unmodified and/or modified sugar moieties, nucleobases, and/or internucleoside linkages, in an oligonucleotide.

"Multi-tissue disease or condition" means a disease or condition affects or is effected by more than one tissue. In treating a multi-tissue disease or condition, it is desirable to affect more than one tissue type. In certain embodiments, treatment of disease or condition may be enhanced by treating the disease or condition in multiple tissues. For example, in certain embodiments, a disease or condition may manifest itself in the liver tissue and the muscle tissue. In certain embodiments, treating the disease or condition in the liver tissue and the muscle tissue will be more effective than treating the disease in either the liver tissue or the muscle tissue.

"Naturally occurring" means found in nature.

"Nucleobase" means an unmodified nucleobase or a modified nucleobase. As used herein a "an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase.

"Oligomeric compound" means a compound consisting of an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 6-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

"Pharmaceutically acceptable salts" means physiologically and pharmaceutically acceptable salts of compounds, i.e., salts that retain the desired biological activity of the parent compound and do not impart undesired toxicological effects thereto.

"Pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

"Phosphorus moiety" means a group of atoms comprising a phosphorus atom. In certain embodiments, a phosphorus moiety comprises a mono-, di-, or tri-phosphate, or phosphorothioate.

"Prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

"RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

"Single-stranded" in reference to an oligomeric compound means such a compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case it would no longer be single-stranded.

"Standard cell assay" means the assay described in Example 1 and reasonable variations thereof.

"Standard in vivo experiment" means the procedure described in Example 2 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Target nucleic acid" means a naturally occurring, identified nucleic acid. In certain embodiments, target nucleic acids are endogenous cellular nucleic acids, including, but not limited to RNA transcripts, pre-mRNA, mRNA, microRNA. In certain embodiments, target nucleic acids are viral nucleic acids. In certain embodiments, target nucleic acids are nucleic acids that an antisense compound is designed to affect.

"Target region" means a portion of a target nucleic acid to which an antisense compound is designed to hybridize.

"TCA motif" means three nucleosides having the nucleobase sequence TCA (5'-3'). Such nucleosides may have modified sugar moieties and/or modified internucleosides linkages. Unless otherwise indicated, the nucleosides of TCA motifs comprise unmodified 2'-deoxy sugar moieties and unmodified phosphodiester internucleoside linkages.

"Terminal group" means a chemical group or group of atoms that is covalently linked to a terminus of an oligonucleotide.

"CNS" means central nervous system. The CNS includes the spine and the brain and the cerebrospinal fluid.

"CNS tissue" means any cell or tissue in the CNS. CNS tissue includes the spine and the brain and the cerebrospinal fluid.

"Cerebrospinal fluid" or "CSF" means the fluid filling the space around the brain and spinal cord.

"Nervous system" means the network of nerve cells and fibers that transmits nerve impulses between parts of the body. The nervous system includes glial cells and neurons. The nervous system includes the central nervous system and the peripheral nervous system.

"Brain target" means a nucleic acid transcript for which there is some desired therapeutic benefit from modulating the amount or activity of the nucleic acid transcript in brain tissue. For example, a given nucleic acid transcript may be expressed in multiple tissues, however one or more therapeutic benefit is achieved when the amount or activity of the target nucleic acid is modulated in brain tissue.

"CNS target" means a nucleic acid transcript for which there is some desired therapeutic benefit from modulating the amount or activity of the nucleic acid transcript in CNS tissue. For example, a given nucleic acid transcript may be expressed in multiple tissues, however one or more therapeutic benefit is achieved when the amount or activity of the target nucleic acid is modulated in CNS tissue.

"Muscle target" means a nucleic acid transcript for which there is some desired therapeutic benefit from modulating the amount or activity of the nucleic acid transcript in muscle tissue. Muscle tissue includes, but is not limited to smooth muscle tissue and skeletal muscle tissue. For example, a given nucleic acid transcript may be expressed in multiple tissues, however one or more therapeutic benefit is achieved when the amount or activity of the target nucleic acid is modulated in muscle tissue.

I. Certain Oligonucleotides

In certain embodiments, the present disclosure provides a compound comprising a half duplex, wherein the half duplex comprises a first oligomeric compound and a second oligomeric compound. In certain embodiments a first oligomeric compound or a second oligomeric compound comprises an oligonucleotide, which consists of linked nucleosides. Oligonucleotides may be unmodified oligonucleotides (RNA or DNA) or may be modified oligonucleotides. Modified oligonucleotides, for example the first modified oligonucleotide or the second modified oligonucleotide, comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$N(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C (=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

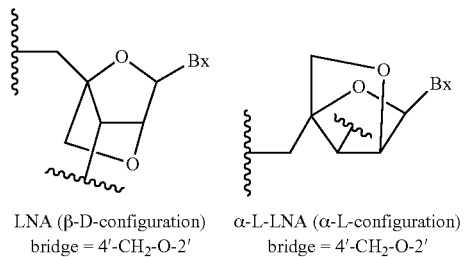

LNA (β-D-configuration)    α-L-LNA (α-L-configuration)
bridge = 4'-CH$_2$-O-2'    bridge = 4'-CH$_2$-O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

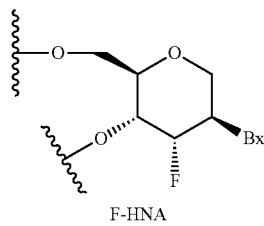

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

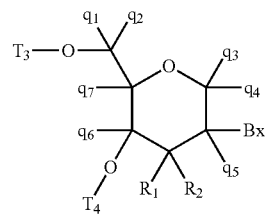

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

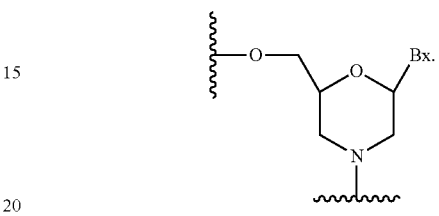

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

1. Certain Modified Nucleobases

In certain embodiments, the first modified oligonucleotide comprises one or more nucleoside comprising an unmodified nucleobase. In certain embodiments, the second modified oligonucleotide comprises one or more nucleoside comprising an unmodified nucleobase. In certain embodiments, modified oligonucleotides, for example the first modified oligonucleotide or the second modified oligonucleotide, comprise one or more nucleoside comprising a modified nucleobase. In certain embodiments, modified oligonucleotides, for example the first modified oligonucleotide or the second modified oligonucleotide, comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C≡C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. In certain embodiments, nucleosides of the first modified oligonucleotide may be linked together using any internucleoside linkage. In certain embodiments, nucleosides of the second modified oligonucleotide may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—$CH_2$—N($CH_3$)—O—$CH_2$—), thiodiester, thionocarbamate (—O—C(=O)(NH)—S—); siloxane (—O—$SiH_2$—O—); and N,N'-dimethylhydrazine (—$CH_2$—N($CH_3$)—N($CH_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

C. Certain Motifs

In certain embodiments, the first modified oligonucleotide comprises one or more modified nucleoside comprising a modified sugar. In certain embodiments, the first modified oligonucleotide comprises one or more modified nucleosides comprising a modified nucleobase. In certain embodiments, the first modified oligonucleotide comprises one or more modified internucleoside linkage. In such embodiments, the modified, unmodified, and differently modified sugar moieties, nucleobases, and/or internucleoside linkages of the first modified oligonucleotide define a pattern or motif. In certain embodiments, the patterns of sugar moieties, nucleobases, and internucleoside linkages are each independent of one another. Thus, the first modified oligonucleotide may be described by its sugar motif, nucleobase motif and/or internucleoside linkage motif (as used herein, nucleobase motif describes the modifications to the nucleobases independent of the sequence of nucleobases).

In certain embodiments, the second modified oligonucleotide comprises one or more modified nucleoside comprising a modified sugar. In certain embodiments, the second modified oligonucleotide comprises one or more modified nucleosides comprising a modified nucleobase. In certain embodiments, the second modified oligonucleotide comprises one or more modified internucleoside linkage. In such embodiments, the modified, unmodified, and differently modified sugar moieties, nucleobases, and/or internucleoside linkages of the second modified oligonucleotide define a pattern or motif. In certain embodiments, the patterns of sugar moieties, nucleobases, and internucleoside linkages are each independent of one another. Thus, the second modified oligonucleotide may be described by its sugar motif, nucleobase motif and/or internucleoside linkage motif (as used herein, nucleobase motif describes the modifications to the nucleobases independent of the sequence of nucleobases).

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides, for example the first modified oligonucleotide or the second modified oligonucleotide, comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiments, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, the second modified oligonucleotide comprises a gapmer-like motif wherein the wings of the gapmer comprise 1-5 nucleosides and the gap of the gapmer comprises 2-6 nucleosides. In certain embodiments, each nucleoside of the gap of a gapmer is an unmodified 2'-deoxy nucleoside. In certain embodiments, the second modified oligonucleotide has a gapmer-like motif that does not support RNase H activity, for example the second modified oligo has RNA-like wings and a DNA-like gap, but the wings, gap, or overall length of the second modified oligonucleotide is insufficient to support RNase H activity.

In certain embodiments, the first modified oligonucleotide comprise or consist of a region having a fully modified sugar motif. In such embodiments, each nucleoside of the fully modified region of the modified oligonucleotide comprises a modified sugar moiety. In certain such embodiments, each nucleoside to the entire first modified oligonucleotide comprises a modified sugar moiety. In certain embodiments, the first modified oligonucleotide comprise or consists of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides (including the first modified oligonucleotide and/or the second modified oligonucleotide) comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides (for example the first modified oligonucleotide or the second modified oligonucleotide) comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine. In certain embodiments, the first modified oligonucleotide has a gapmer motif. In certain embodiments, the first modified oligonucleotide has a gapmer motif and the second modified oligonucleotide does not have a gapmer motif. In certain embodiments, the first modified oligonucleotide has a gapmer motif and the second modified oligonucleotide has a fully modified motif.

3. Certain Internucleoside Linkage Motifs

In certain embodiments, oligonucleotides, for example the first modified oligonucleotide and/or the second modified oligonucleotide, comprise modified and/or unmodified internucleoside linkages arranged along the oligonucleotide or region thereof in a defined pattern or motif. In certain embodiments, essentially each internucleoside linking group is a phosphate internucleoside linkage (P═O). In certain embodiments, each internucleoside linking group of a modified oligonucleotide is a phosphorothioate (P═S). In certain embodiments, essentially each internucleoside linking group of the first modified oligonucleotide is a phosphate internucleoside linkage (P═O). In certain embodiments, each internucleoside linking group of the first modified oligonucleotide is a phosphorothioate (P═S). In certain embodiments, essentially each internucleoside linking group of the second modified oligonucleotide is a phosphate internucleoside linkage (P═O). In certain embodiments, each internucleoside linking group of the second modified oligonucleotide is a phosphorothioate (P═S). In certain embodiments, each internucleoside linking group of the first modified oligonucleotide is independently selected from a phosphorothioate and phosphate internucleoside linkage. In certain embodiments, each internucleoside linking group of the second modified oligonucleotide is independently selected from a phosphorothioate and phosphate internucleoside linkage. In certain embodiments, the sugar motif of the first modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of the second modified oligonucleotide is gapmer-like and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, the first modified oligonucleotide can have any of a variety of ranges of lengths. In certain embodiments, the second modified oligonucleotide can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, oligonucleotides consist of 6 to 7, 6 to 8, 6 to 9, 6 to 10, 6 to 11, 6 to 12, 7 to 8, 7 to 9, 7 to 10, 7 to 11, 7 to 12, 8 to 9, 8 to 10, 8 to 11, 8 to 12, 9 to 10, 9 to 11, 9 to 12, 10 to 11, 10 to 12, 11 to 12, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

E. Certain Modified Oligonucleotides

In certain embodiments, the above modifications (sugar, nucleobase, internucleoside linkage) are incorporated into a first modified oligonucleotide, a second modified oligonucleotide, or both a first modified oligonucleotide and a second modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified or a first modified oligonucleotide or a second modified oligonucleotide) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides, including a first modified oligonucleotide or a second modified oligonucleotide, are covalently attached to one or more conjugate groups. In certain embodiments, a second modified oligonucleotide is covalently attached to one or more conjugate groups. In certain embodiments, a second modified oligonucleotide is covalently attached to one or more conjugate groups and the first modified oligonucleotide is not attached to a conjugate group. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to form a bond with to a particular site on a parent compound and the other is selected to form a bond with to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Compounds

In certain embodiments, the present invention provides antisense compounds, which comprise or consist of an oligomeric compound comprising an antisense oligonucleotide, having a nucleobase sequence complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified and optionally comprises a conjugate group. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

IV. Certain Half Duplexes

In certain embodiments, the present disclosure provides half duplex oligomeric compounds and half duplex antisense compounds. Half duplex oligomeric compounds have a first modified oligonucleotide and a second modified oligonucleotide, wherein the first modified oligonucleotide is 14-30 linked nucleosides and has a nucleobase sequence complementary to the nucleobase sequence of the second oligomeric compound and to a nucleic acid target, and wherein the second modified oligonucleotide has between 6-12 linked nucleosides. In a half duplex, the second oligomeric compound is shorter than the first oligomeric compound. For example, in certain embodiments, the second oligomeric compound is 5, 6, 7, 8, 9, 10, 11, 12, 13, or 14 nucleobases shorter in length than the first oligomeric compound.

In certain embodiments, the first modified oligonucleotide is complementary to a target nucleic acid. In certain such embodiments, the first modified oligonucleotide is a gapmer as described above. Thus, in such embodiments, the first oligomeric compound is capable of hybridizing to a target nucleic acid and eliciting cleavage of the target nucleic acid by RNase H. In certain such embodiments, the first modified oligonucleotide is fully modified and does not elicit cleavage of a target nucleic acid via RNase H. In certain such embodiments, the first modified oligonucleotide is fully modified and is capable of modulating splicing of a given target nucleic acid.

In certain such embodiments, the second oligomeric compound improves a property of the first oligomeric compound compared to the property in the absence of the second, shorter oligomeric compound. In certain such embodiments, the second oligomeric compound improves a property of the first oligomeric compound compared to the property where the second oligomeric compound is of equal or greater length than the first oligomeric compound. In certain embodiments, the improved property is one or more of distribution to a target tissue, uptake into a target cell, potency, and/or efficacy. In certain embodiments, the improved property is penetration of the blood brain barrier. In certain embodiments, the improved property is penetration of the blood brain barrier which allows systemic administration of a half duplex in order to reduce a target nucleic acid in the CNS tissue. In certain embodiments, the target tissue is in the CNS. In certain embodiments, the target tissue is muscle tissue. In certain embodiments, the target tissue is other than liver (extra-hepatic). In certain embodiments, it is desirable to reduce target in more than one tissue. In certain such embodiments, it is desirable to reduce target in the liver and one or more other tissues. In certain embodiments, it is desirable to reduce target in more than one extra-hepatic tissue.

In certain embodiments, the first oligonucleotide of a half duplex is a gapmer. In certain such embodiments, the wings of the gapmer comprise 2'-MOE modified nucleosides. In certain embodiments, the wings of the gapmer comprise cEt nucleosides. In certain embodiments the wings of the gapmer comprise LNA nucleosides. In certain embodiments, the wings of a gapmer comprise at least one 2'-MOE modified nucleoside and at least one bicyclic nucleoside. In certain such embodiments, each such bicyclic nucleoside is selected from among an LNA nucleoside and a cEt nucleoside. In certain embodiments, the gap constitutes 7-10 2'-deoxynucleosides.

In certain embodiments, the second oligonucleotide of the half duplex has a motif consisting of cEt nucleosides and DNA nucleosides. For example, the second oligonucleotide may have an A-B-C motif, wherein A and C are RNA-like nucleosides and B is DNA-like nucleosides. In certain embodiments, A and C are selected from either cEt or LNA and B is one or more 2'-deoxynucleosides. In certain embodiments, the second oligonucleotide of the half duplex has an A-B-C motif selected from 4-2-3, 2-4-2, and 3-2-4. In certain embodiments, the second oligonucleotide comprises at least one bicyclic nucleoside. In certain embodiments, the bicyclic nucleoside is selected from cEt or LNA. In certain embodiments, the second oligonucleotide of the half duplex has one or more 2'-deoxynucleosides.

In certain embodiments, the second oligonucleotide comprises at least one 2'-MOE nucleoside. In certain embodiments, the second oligonucleotide comprises 2'-MOE and 2'-deoxynucleosides. In certain embodiments, the second oligonucleotide comprises at least one bicyclic nucleoside.

In certain embodiments, the second oligonucleotide comprises at least one cEt nucleoside. In certain embodiments, the second oligonucleotide comprises at least one LNA nucleoside. In certain embodiments, the second oligonucleotide comprises cEt and 2'-deoxynucleosides. In certain embodiments, the second oligonucleotide has sugar motif of alternating modification types (including no modification). In certain such embodiments, the sugar motif of the second oligonucleotide alternates between 2'-MOE nucleosides and 2'-deoxynucleosides. In certain such embodiments, the sugar motif of the second oligonucleotide alternates between cEt nucleosides and 2'-deoxynucleosides. In certain embodiments, the second oligonucleotide has a sugar motif similar to a gapmer (as described above) except that it may not elicit cleavage of a target nucleic acid. Such gapmer-like motifs have a central region and flanking wing regions. In certain such embodiments, the central region is comprised of 2'-deoxynucleosides and the wing regions are cEt modified nucleosides. In certain such embodiments, the central region is comprised of 2'-deoxynucleosides and the wing regions are LNA modified nucleosides. In certain embodiments, the central region is comprised of 2'-deoxynucleosides and the wing regions are 2'-MOE modified nucleosides. The internucleoside linkages of the second oligonucleotide may be modified or phosphodiester. In certain embodiments, the internucleoside linkages of the second oligonucleotide follow a gapmer-like motif—phosphorothioate wings and phosphodiester in the center. Such internucleoside linkage motif may or may not track the sugar motif.

In certain embodiments, at least one of the first and second oligomeric compounds comprises a conjugate group (as described above). Typically, the second oligomeric compound comprises a conjugate group. The conjugate group may be attached at either the 3'- or 5'-end of the oligomeric compound. In certain embodiments, a conjugate group is attached to both ends.

V. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligomeric compounds of antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

B. Certain Target Nucleic Acids in Certain Tissues

In certain embodiments, antisense compounds comprise or consist of an oligonucleotide comprising a region that is complementary to a target nucleic acid, wherein the target nucleic acid is expressed in an extra-hepatic tissue. Extra-hepatic tissues include, but are not limited to: skeletal muscle, cardiac muscle, smooth muscle, adipose, white adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, pancreas, and colon. Extra-hepatic tissues include, but are not limited to CNS tissues, for example, the brain.

I. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

NONLIMITING DISCLOSURE AND
INCORPORATION BY REFERENCE

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Synthesis of Cholesterol-Conjugated Oligonucleotides

Selected modified oligonucleotides are described in the table below. Modified oligonucleotides were synthesized by standard solid phase oligonucleotide synthesis procedures well known in the art. Modified oligonucleotides are 100% complementary to the DMPK gene, the complement of GENBANK NO: NT_011109.15 truncated from 18540696_18555106 (antisense) (SEQ ID NO: 1) or have 100% sequence identity with the DMPK gene, the complement of GENBANK NO: NT_011109.15 truncated from 18540696_18555106 (sense), except for 819733, which has a TCA linker on the 5' end before the portion of the oligonucleotide that is 100% complementary to the complement of GENBANK NO: NT_011109.15 truncated from 18540696_18555106. Duplexes were formed by annealing the first and second purified single stranded oligonucleotides together to form a duplex.

CholTEG (5' to 3' notation) and TEGChol (3' to 5' notation) refer to this structure:

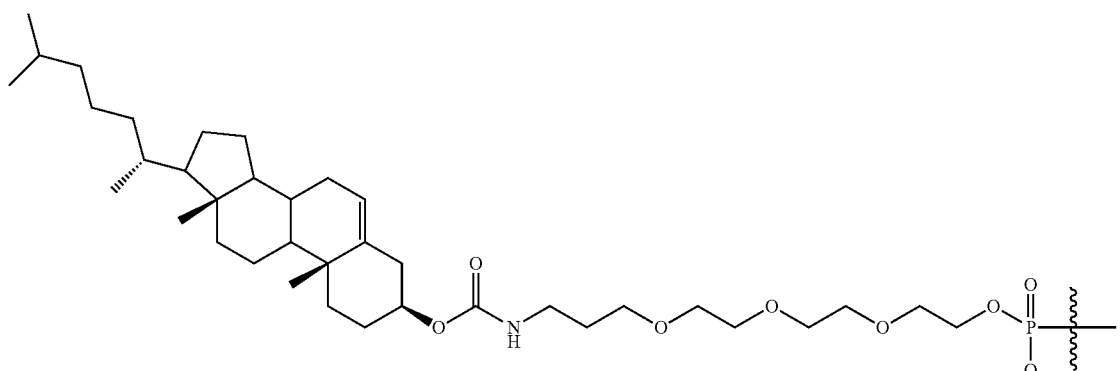

3TEGChol (5' to 3' notation) and TEG3Chol (3' to 5' notation) refer to this structure:

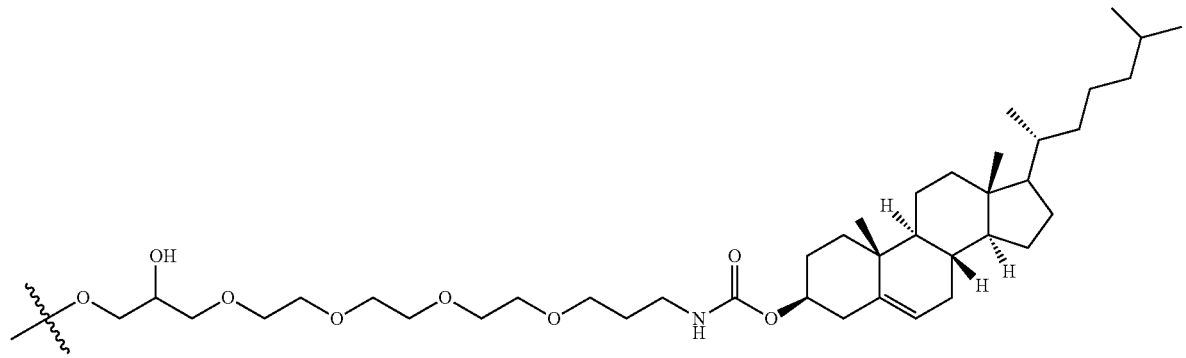 [SMILES: *OCC(O)COCCOCCOCCOCCCNC(=O)O[C@H]1CC[C@@]2(C)C(=CC[C@@H]3[C@@H]2CC[C@]2(C)C([C@H](C)CCCC(C)C)CC[C@@H]32)C1]

TABLE 1

Modified oligonucleotides

| Compound ID | Chemistry notation (5'-3') | Strand | SEQ ID NO |
|---|---|---|---|
| 486178 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | antisense | 2 |
| 819733 | CholTEG-$T_{do}{}^mC_{do}A_{do}$ $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | antisense | 3 |
| 1055617 | CholTEG-${}^mC_{ko}{}^mC_{ko}T_{do}{}^mC_{do}G_{do}G_{do}T_{ko}A_k$ | sense | 4 |
| 1055618 | ${}^mC_{ko}{}^mC_{ko}T_{do}{}^mC_{do}G_{do}G_{do}T_{ko}A_{ko}$-3TEGChol | sense | 4 |
| 1055619 | CholTEG-$A_{ko}T_{ko}T_{ko}T_{ko}A_{do}T_{do}T_{ko}G_{ko}T_k$ | sense | 5 |
| 1055620 | $A_{ko}T_{ko}T_{ko}T_{ko}A_{do}T_{do}T_{ko}G_{do}T_{ko}$-3TEGChol | sense | 5 |
| 1017273 | CholTEG-$C_{ms}C_{ms}U_{ms}C_{ro}G_{ro}G_{ro}U_{ro}A_{ro}U_{ro}U_{ro}U_{ro}A_{ro}U_{ro}U_{ms}G_{ms}U_m$ | sense | 6 |
| 1057287 | CholTEG- $T_{ko}T_{ko}G_{ko}T_{ko}G_{do}T_{do}T_{do}{}^mC_{do}A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_{ks}$ | both | 7 |
| 1057757 | $A_{ks}C_{ks}A_{ks}A_{ds}T_{ds}A_{ds}A_{ds}A_{ds}T_{ds}{}^mC_{ds}{}^mC_{ds}G_{ds}A_{ks}G_{ks}G_{ds}G_{do}T_{do}T_{do}{}^mC_{do}{}^mC_{ko}{}^mC_{ko}T_{ko}{}^mC_{ko}$-3TEGChol | both | 8 |

CholTEG and 3TEGChol represent cholesterol subunits as described above. Subscripts in the table above: "s" represents a phosphorothioate internucleoside linkage, "o" represents a phosphate internucleoside linkage, "m" represents a 2'-o-methyl nucleoside, "r" represents a ribose nucleoside, "d" represents a 2'-deoxynucleoside, "k" represents a 2'-constrained ethyl nucleoside.
Superscripts: "m" before a C represents a 5-methylcytosine.

TABLE 2

Pre-formed duplexes

| Duplex | | SEQ ID NO |
|---|---|---|
| 416178/1055617 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 2 |
| | $A_{ko}T_{ko}G_{do}G_{do}{}^mC_{do}T_{do}{}^mC_{ko}{}^mC_k$-TEGchol | 4 |
| 416178/1055618 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 2 |
| | 3TEGchol-${}_oA_{ko}T_{ko}G_{do}G_{do}{}^mC_{do}T_{do}{}^mC_{ko}{}^mC_k$ | 4 |
| 416178/1055619 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 2 |
| | $T_{ko}G_{ko}T_{ko}T_{do}A_{do}T_{ko}T_{ko}T_{ko}A_k$-TEGchol | 5 |
| 416178/1017273 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 2 |
| | $U_{ms}G_{ms}U_{mo}U_{ro}A_{ro}U_{ro}U_{ro}U_{ro}A_{ro}U_{ro}G_{ro}G_{ro}C_{rs}U_{ms}C_{ms}C_m$-TEGchol | 6 |

TABLE 2-continued

Pre-formed duplexes

| Duplex | | SEQ ID NO |
|---|---|---|
| 1057287 | $T_{do}$($^mC_{do}A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ / $T_{do}G_{do}T_{ko}G_{ko}T_{ko}T_k$-TEGchol) | 9 |
| 1057757 | $A_{ks}C_{ks}A_{ks}A_{ds}T_{ds}A_{ds}A_{ds}A_{ds}T_{ds}{}^mC_{ds}{}^mC_{ds}G_{ds}A_{ks}G_{ks}G_{ks}$($G_{do}$ / 3TEGChol-$_o{}^mC_{ko}T_{ko}{}^mC_{ko}{}^mC_{ko}{}^mC_{do}{}^mT_{do}{}^mT_d$) | 8 |

Example 2: Activity of Modified Oligonucleotides and Half-Duplexes Targeted to DMPK in Mouse Muscle Treatment Modified oligonucleotides described above were tested in mice to assess the activity and tolerability of the oligonucleotides. Wild type BALB/c mice were administered single oligonucleotides or duplexes at 5, 6, 10 or 20 mg/kg/week once a week for 4 weeks via intravenous injection as indicated in the tables below. Each treatment group consisted of 4 mice. A group of four mice received PBS as a negative control. Animals were sacrificed 48 hours after the final dose. The quadricep was collected from each animal, and RT-PCR was performed. Results are normalized to GADPH and presented relative to PBS control. "Not tolerated" means that after physical observation of one or more indicators of toxicity, the mice were removed from the study. The half duplex compounds showed improved tolerability compared to a single-strand analog and increased activity and tolerability compared to hairpin analogs. The half duplex compounds also showed increased activity in muscle tissue compared to full duplex analogs.

TABLE 3

DMPK levels in quadricep

| Compound ID | Type | Conjugate group/linker | Dose (mg/kg/wk) | DMPK % control |
|---|---|---|---|---|
| PBS | n/a | n/a | n/a | 100 |
| 486178 | single stranded | none | 6 | n.d. |
| 819733 | single stranded | 5'-cholTEG-TCA | 6 | 21 |
| 1057287 | ss/hairpin | 5'-cholTEG | 6 | 53 |
| 1057757 | ss/hairpin | 3'-chol | 6 | 27 |
| 416178/ 1055617 | half duplex | 5'-cholTEG on sense strand | 6 | 23 |
| 416178/ 1055618 | half duplex | 3'-chol on sense strand | 6 | 25 |
| 416178/ 1055619 | half duplex | 5'-cholTEG on sense strand | 6 | 16 |
| 486178 | single stranded | none | 20 | 32 |
| 819733 | single stranded | 5'-cholTEG-TCA | 20 | not tolerated |
| 1057287 | ss/hairpin | 5'-cholTEG | 20 | not tolerated |

TABLE 3-continued

DMPK levels in quadricep

| Compound ID | Type | Conjugate group/linker | Dose (mg/kg/wk) | DMPK % control |
|---|---|---|---|---|
| 1057757 | ss/hairpin | 3'-chol | 20 | not tolerated |
| 416178/ 1055617 | half duplex | 5'-cholTEG on sense strand | 20 | 3 |
| 416178/ 1055618 | half duplex | 3'-chol on sense strand | 20 | 4 |
| 416178/ 1055619 | half duplex | 5'-cholTEG on sense strand | 20 | 2 |

TABLE 4

DMPK levels in quadricep

| Compound ID | Type | Conjugate group | Dose (mg/kg/wk) | DMPK % control |
|---|---|---|---|---|
| PBS | n/a | n/a | n/a | 100 |
| 486178 | single stranded | none | 5 | 67 |
| 819733 | single stranded | 5'-chol-TCA | 5 | 26 |
| 486178/ 1017273 | full duplex | 5'-chol on sense strand | 5 | 60 |
| 486178 | single stranded | none | 10 | 53 |
| 819733 | single stranded | 5'-chol-TCA | 10 | 9 |
| 486178/ 1017273 | full duplex | 5'-chol on sense strand | 10 | 30 |
| 486178 | single stranded | none | 20 | 29 |
| 819733 | single stranded | 5'-chol-TCA | 20 | not tolerated |
| 486178/ 1017273 | full duplex | 5'-chol on sense strand | 20 | 7 |

Example 3: Synthesis of Cholesterol-Conjugated Oligonucleotides

Selected modified oligonucleotides are described in the table below and were synthesized according to the methods described in Example 1.

TABLE 5

Modified oligonucleotides

| Compound ID | Chemistry notation (5'-3') | Strand | SEQ ID NO |
|---|---|---|---|
| 1011771 | CholTEG-$^mC_{es}{}^mC_{es}T_{es}{}^mC_{do}G_{do}G_{do}T_{do}A_{do}T_{do}T_{do}T_{do}A_{do}T_{ds}T_{es}G_{es}T_e$ | Sense | 10 |
| 1054602 | CholTEG-$T_{do}{}^mC_{do}A_{do}C_{ms}C_{ms}U_{ms}C_{ro}G_{ro}G_{ro}U_{ro}A_{ro}U_{ro}U_{ro}U_{ro}A_{ro}U_{ro}U_{ms}G_{ms}U_m$ | Sense | 11 |
| 1073756 | $G_{ms}C_{ms}U_{ms}C_{ro}G_{ro}G_{ro}U_{ro}A_{ro}U_{ro}U_{ro}U_{ro}A_{ro}U_{ro}U_{ms}G_{ms}U_m$ | Sense | 12 |

Subscripts in the table above: "s" represents a phosphorothioate internucleoside linkage, "o" represents a phosphate internucleoside linkage, "m" represents a 2'-o-methyl nucleoside, "r" represents a ribose nucleoside, "d" represents a 2'-deoxynucleoside, "k" represents a 2'-constrained ethyl nucleoside. Superscripts: "m" before a C represents a 5-methylcytosine.

Example 4: Acute Tolerability of Modified Oligonucleotides and Half-Duplexes Targeted to DMPK Treatment Modified oligonucleotides described above were tested in mice to assess the tolerability of the oligonucleotides. Wild type BALB/c mice were administered single oligonucleotides or duplexes at 24 mg/kg via intravenous injection as indicated in the tables below. Each treatment group consisted of 4 mice. A group of four mice received PBS as a negative control. Animals were sacrificed 1 hour after receiving the 24 mg/kg injection. The animals were also observed after receiving the 24 mg/kg injection. "Lethargic, spinning" means that after physical observation the mice were much less active than the control group and exhibited a lack of balance including an inability to self right and repeated rolling. The half duplex compounds showed improved tolerability compared to a single-strand analog. The half duplex compounds also showed improved tolerability compared to full duplex analogs.

TABLE 6

Acute Tolerability of modified oligonucleotides and half-duplexes targeted to DMPK

| Compound ID | Type | Conjugate group | Observation |
|---|---|---|---|
| PBS | Control | | Normal |
| 486178 | Parent | None | Normal |
| 819733 | Single strand | Cholesterol | Lethargic, spinning |
| 416178/1055619 | half duplex | 5'-chol TEG on sense strand | Normal |
| 416178/1055617 | half duplex | 3'-chol on sense strand | Normal |
| 819933/1073756 | Full duplex | 5'-chol on antisense strand | Lethargic, spinning |
| 468178/1054602 | Full duplex | 5'-chol on sense strand | Lethargic, spinning |
| 468178/1017273 | Full Duplex | 5'-chol on sense strand | Lethargic, spinning |
| 468178/1011771 | Full Duplex | 5'-chol on sense strand | Normal |

Example 5: Synthesis of Cholesterol-Conjugated Oligonucleotides

Selected modified oligonucleotides are described in the table below and were synthesized according to the methods described in Example 1.

Modified oligonucleotides targeted to Malat-1

| Compound ID | Chemistry notation (5'-3') | Strand | SEQ ID NO |
|---|---|---|---|
| 556007 | $^mC_{ks}T_{ks}A_{ks}G_{ds}T_{ds}T_{ds}{}^mC_{ds}A_{ds}{}^mC_{ds}T_{ds}G_{ds}A_{ds}A_{ds}T_{ks}G_{ks}{}^mC_k$ | antisense | 13 |
| 1166384 | CholTEG-$G_{ko}C_{ko}A_{ko}T_oT_oC_{ko}A_{ko}G_k$ | sense | 14 |
| 1166383 | CholTEG-$G_{ko}T_{ko}G_{ko}A_{ko}A_oC_oT_{ko}A_{ko}G_k$ | sense | 15 |
| 1188901 | CholTEG-$T_{ko}G_{ko}A_{ko}A_oC_oT_{ko}A_{ko}G_k$ | sense | 16 |
| 1194726 | CholTEG-$T_{ks}G_{ks}A_{ks}A_sC_sT_{ks}A_{ks}G_k$ | sense | 16 |
| 1194723 | CholTEG-$C_{ms}A_{ms}G_{ms}U_{rs}G_{rs}A_{rs}A_{rs}C_{rs}U_{ms}A_{ms}G_m$ | sense | 17 |
| 1194722 | CholTEG-$C_{mo}A_{mo}G_{mo}U_{ro}G_{ro}A_{ro}A_{ro}C_{ro}U_{mo}A_{mo}G_m$ | sense | 17 |
| 1166379 | CholTEG-$C_{ko}T_{ko}A_{ko}G_{ko}T_oT_oG_{ko}C_{ko}A_{ko}T_k$ | sense | 18 |

Subscripts in the table above: "s" represents a phosphorothioate internucleoside linkage, "o" represents a phosphate internucleoside linkage, "m" represents a 2'-o-methyl nucleoside, "r" represents a ribose nucleoside, "d" represents a 2'-deoxynucleoside, "k" represents a 2'-constrained ethyl nucleoside. Superscripts: "m" before a C represents a 5-methylcytosine. "CholTEG" has the meaning described above.

Example 6: Activity of Systemically Administered Modified Oligonucleotides and Half-Duplexes Targeted to Malat-1

Modified oligonucleotides described above were tested in mice to assess the activity of the oligonucleotides in various tissues. As described above, Compound 556007 is a single-stranded oligonucleotide complementary to the Malat-1 transcript. Compound 556007 is complementary to the Malat-1 gene, the complement of GENBANK NO: NT_082868.4 truncated from 2689000_2699000 (SEQ ID NO: 19). Compounds 1166384, 1166383, 1188901, 1194726, 1194723, 1194722, and 1166379 are complementary to Compound 556007. Compound 556007 was annealed to each of Compounds 1166384, 1166383, 1188901, 1194726, 1194723, 1194722, and 1166379 to form the half duplexes described in the table below. These half-duplexes were then administered to mice.

Treatment

Wild type BALB/c mice were administered single dose of a half duplex at either 7 mg/kg/wk or 50 mg/kg/wk once a week for 4 weeks via intravenous injection as indicated in the tables below. Each treatment group consisted of 4 mice. A group of four mice received PBS as a negative control. Animals were sacrificed 72 hours after the final dose. Tissue from the cortex, spinal cord, striatum, cerebeullum, liver, retina, kidney, and quadricep was collected from each animal, and RT-PCR was performed. Results are normalized to GADPH and presented relative to PBS control. The half duplex compounds showed improved activity in the CNS after systemic dosing compared to a single-stranded oligonucleotide alone.

TABLE 8

Half Duplex Activity in CNS Tissue

| Compound ID | Dose | Cortex | Spinal Cord | Striatum | Cerebellum |
|---|---|---|---|---|---|
| PBS | NA | 100 | 100 | 100 | 100 |
| 556007 | 50 | 91 | 95 | 82 | 96 |
|  | 7 | 118 | 115 | 92 | 101 |
| 556007/1166384 | 50 | 61 | 67 | 59 | 79 |
|  | 7 | 93 | 100 | 104 | 86 |
| 556007/1166383 | 50 | 46 | 33 | 42 | 64 |
|  | 7 | 91 | 79 | 104 | 87 |
| 556007/1188901 | 50 | 36 | 44 | 48 | 71 |
|  | 7 | 89 | 97 | 96 | 93 |
| 556007/1194723 | 50 | 64 | 53 | 51 | 80 |
|  | 7 | 105 | 92 | 104 | 91 |
| 556007/1194722 | 50 | 70 | 67 | 65 | 74 |
|  | 7 | 102 | 91 | 105 | 99 |
| 556007/1166379 | 50 | 95 | 97 | 83 | 94 |
|  | 7 | 91 | 107 | 77 | 89 |

TABLE 9

Half Duplex Activity in Various Tissue

| Compound ID | Dose | Liver | Retina | Kidney | Quad |
|---|---|---|---|---|---|
| PBS | NA | 100 | 100 | 100 | 100 |
| 556007 | 50 | 6 | 55 | 31 | 4 |
|  | 7 | 17 | 105 | 18 | 12 |
| 556007/1166384 | 50 | 7 | 44 | 33 | 3 |
|  | 7 | 8 | 90 | 28 | 9 |
| 556007/1166383 | 50 | 5 | 44 | 32 | 3 |
|  | 7 | 10 | 97 | 22 | 11 |
| 556007/1188901 | 50 | 2 | 22 | 9 | 2 |
|  | 7 | 4 | 63 | 13 | 6 |
| 556007/1194723 | 50 | 4 | 68 | 12 | 2 |
|  | 7 | 6 | 118 | 25 | 8 |
| 556007/1194722 | 50 | 3 | 61 | 12 | 2 |
|  | 7 | 6 | 109 | 37 | 10 |
| 556007/1166379 | 50 | 4 | 74 | 25 | 3 |
|  | 7 | 7 | 103 | 38 | 10 |

The invention claimed is:

1. A compound comprising a first oligomeric compound and a second oligomeric compound, wherein the first oligomeric compound comprises a first modified oligonucleotide consisting of 14-20 linked nucleosides and has a nucleobase sequence complementary to the nucleobase sequence of the second oligomeric compound and to a nucleic acid target; and the second oligomeric compound comprises a second modified oligonucleotide consisting of 6-12 linked nucleosides;

wherein the first modified oligonucleotide has a sugar motif comprising:
a 5'-region consisting of 1-5 linked 5'-nucleosides,
a central region consisting of 6-10 linked central region nucleosides, and a 3'-region consisting of 1-5 linked 3'-nucleosides;
wherein
each of the 5'-region nucleosides and each of the 3'-region comprises a modified sugar moiety and each of the central region nucleosides comprises an unmodified DNA sugar moiety; and
wherein the second modified oligonucleotide has a sugar motif comprising:
a 5'-region consisting of 2-4 linked 5'-nucleosides,
a central region consisting of 2-4 linked central region nucleosides, and
a 3'-region consisting of 2-4 linked 3'-nucleosides; wherein
each of the 5'-region nucleosides and each of the 3'-region comprises a modified sugar moiety and each of the central region nucleosides comprises an unmodified DNA sugar moiety.

2. The compound of claim 1, wherein the first modified oligonucleotide has a nucleobase sequence that is at least 80%, at least 90%, or 100% complementary to the nucleobase sequence of the target nucleic acid, when measured across the entire nucleobase sequence of the first modified oligonucleotide.

3. The compound of claim 1, wherein the first modified oligonucleotide comprises at least 5, at least 6, at least 7, or at least 8 contiguous linked 2'-deoxynucleosides.

4. The compound of claim 1, wherein the first modified oligonucleotide and/or the second modified oligonucleotide comprises at least one modified nucleoside comprising a bicyclic sugar moiety.

5. The compound of claim 1, wherein the first modified oligonucleotide and/or the second modified oligonucleotide comprises at least one modified nucleoside comprising a bicyclic sugar moiety selected from cEt and LNA.

6. The compound of claim 1, wherein the first modified oligonucleotide and/or the second modified oligonucleotide comprises at least one modified nucleoside comprising a non-bicyclic sugar moiety comprising a 2'-MOE or 2'-OMe.

7. The compound of claim 1, wherein the first modified oligonucleotide and/or the second modified oligonucleotide comprises at least one modified nucleoside comprising a sugar surrogate selected from a morpholino, a PNA, a F-HNA, a THP, or a modified THP.

8. The compound of claim 1, wherein the first modified oligonucleotide has a sugar motif comprising:
a 5'-region consisting of 5 linked 5'-nucleosides,
a central region consisting of 10 linked central region nucleosides, and
a 3'-region consisting of 5 linked 3'-nucleosides; or
a 5'-region consisting of 3 linked 5'-nucleosides,
a central region consisting of 10 linked central region nucleosides, and
a 3'-region consisting of 3 linked 3'-nucleosides;
wherein each of the 5'-region nucleosides and each of the 3'-region comprises a modified sugar moiety and each of the central region nucleosides comprises an unmodified DNA sugar moiety.

9. The compound of claim 1, wherein the first modified oligonucleotide consists of 14-20, 16-20, 16-18, 16, or 20 linked nucleosides.

10. The compound of claim 1, wherein the first modified oligonucleotide and/or the second modified oligonucleotide comprises at least one modified internucleoside linkage.

11. The compound of claim 10, wherein each internucleoside linkage of the first modified oligonucleotide and/or the second modified oligonucleotide is a modified internucleoside linkage.

12. The compound of claim 10 wherein at least one internucleoside linkage of the first oligonucleotide and/or the second modified oligonucleotide is a phosphorothioate internucleoside linkage.

13. The compound of claim 12 wherein the first modified oligonucleotide and/or the second modified oligonucleotide comprises at least one unmodified phosphodiester internucleoside linkage.

14. The compound of claim 11, wherein each internucleoside linkage of the first oligonucleotide is a phosphorothioate internucleoside linkage.

15. The compound of claim 1, wherein the second modified oligonucleotide is at least 75%, at least 80%, at least 90%, or 100% complementary to the first modified oligonucleotide, over the length of the second modified nucleotide.

16. The compound of claim 1, wherein the second modified oligonucleotide has a sugar motif comprising:
a 5'-region consisting of 2 linked 5'-nucleosides,
a central region consisting of 4 linked central region nucleosides, and
a 3'-region consisting of 2 linked 3'-nucleosides; or
a 5'-region consisting of 4 linked 5'-nucleosides,
a central region consisting of 2 linked central region nucleosides, and
a 3'-region consisting of 3 linked 3'-nucleosides;
wherein each of the 5'-region nucleosides and each of the 3'-region comprises a modified sugar moiety and each of the central region nucleosides comprises an unmodified DNA sugar moiety.

17. The compound of claim 1, wherein the second modified oligonucleotide consists of 6-10, 7-10, 8-10, 8-9, 7-9, 8, or 9 linked nucleosides.

18. The compound of claim 1, wherein the first modified oligonucleotide or the second modified oligonucleotide comprises at least one modified nucleobase.

19. The compound of claim 18, wherein the modified nucleobase is a 5'-Me cytosine.

20. The compound of claim 1, wherein the 3'-most nucleobase of the second modified oligonucleotide is complementary to the 5'-most nucleobase of the first modified oligonucleotide.

21. The compound of claim 1, wherein the compound comprises a conjugate group covalently attached to the first modified oligonucleotide or the second modified oligonucleotide.

22. The compound of claim 21, wherein the conjugate group is covalently attached to the 3'-end or the 5'-end of the first modified oligonucleotide or the second modified oligonucleotide.

23. The compound of claim 21, wherein the conjugate group consists of a conjugate linker and a conjugate moiety.

24. The compound of claim 23, wherein the conjugate moiety is a lipid, a $C_{16}$ alkyl, or cholesterol.

25. The compound of claim 23, wherein the conjugate linker is TCA, TEG, or hexylamino.

26. The compound of claim 1, where the compound exists primarily as a duplex at or below 57° C., at or below 47° C., or at 37° C.

27. A pharmaceutical composition comprising the compound of claim 1 and a pharmaceutically acceptable carrier or diluent.

28. A method comprising administering to an animal the compound of claim 1.

29. A method of treating a disease associated with an extra-hepatic nucleic acid target comprising administering to an individual having or at risk for developing a disease associated with the extra-hepatic nucleic acid target a therapeutically effective amount of the compound of claim 1; and thereby treating the disease associated with the extra-hepatic nucleic acid target.

30. The method of claim 29, wherein the extra-hepatic nucleic acid target is a muscle target.

31. The method of claim 29, wherein the extra-hepatic nucleic acid target is DMPK.

32. The method of claim 29, wherein the extra-hepatic nucleic acid target is a CNS target.

33. The method of claim 29, wherein the administration is intrathecal or non-parenteral.

* * * * *